United States Patent
Wood et al.

(10) Patent No.: US 10,527,507 B2
(45) Date of Patent: Jan. 7, 2020

(54) ARTIFICIAL SKIN AND ELASTIC STRAIN SENSOR

(71) Applicant: President and Fellows of Harvard College, Cambridge, MA (US)

(72) Inventors: Robert J. Wood, Cambridge, MA (US); Yong-Lae Park, Cambridge, MA (US); Carmel S. Majidi, Pittsburgh, PA (US); Bor-rong Chen, Medford, MA (US); Leia Stirling, Stoneham, MA (US); Conor James Walsh, Dublin (IE); Radhika Nagpal, Cambridge, MA (US); Diana Young, Boston, MA (US); Yigit Menguc, Somerville, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 15/823,030

(22) Filed: Nov. 27, 2017

(65) Prior Publication Data
US 2018/0143091 A1 May 24, 2018

Related U.S. Application Data

(63) Continuation of application No. 14/346,853, filed as application No. PCT/US2012/056903 on Sep. 24, 2012, now Pat. No. 9,841,331.
(Continued)

(51) Int. Cl.
*G01L 1/22* (2006.01)
*B25J 13/08* (2006.01)
(Continued)

(52) U.S. Cl.
CPC .............. *G01L 1/22* (2013.01); *A43B 13/203* (2013.01); *A43B 23/029* (2013.01);
(Continued)

(58) Field of Classification Search
CPC ....... G01L 1/22; A43B 13/203; A43B 13/029; A61B 5/1036
(Continued)

(56) References Cited

U.S. PATENT DOCUMENTS 3,789,511 A 2/1974 Groom et al.
4,014,217 A 3/1977 Lagasse et al.
(Continued)

FOREIGN PATENT DOCUMENTS

CN 101839703 A 9/2010
JP H01103281 A 4/1989
(Continued)

OTHER PUBLICATIONS

Noda, E. Iwase, K. Matsumoto, I. Shimoyama. "Stretchable liquid tactile sensor for robot joint". IEEE International Conference on Robotics and Automation. May 2010. pp. 4212-4217.*
(Continued)

*Primary Examiner* — Tarun Sinha
(74) *Attorney, Agent, or Firm* — Nixon Peabody LLP; Ronald I. Eisenstein; David S. Resnick

(57) ABSTRACT

An elastic strain sensor can be incorporated into an artificial skin that can sense flexing by the underlying support structure of the skin to detect and track motion of the support structure. The unidirectional elastic strain sensor can be formed by filling two or more channels in an elastic substrate material with a conductive liquid. At the ends of the channels, a loop port connects the channels to form a serpentine channel. The channels extend along the direction of strain and the loop portions have sufficiently large cross-sectional area in the direction transverse to the direction of strain that the sensor is unidirectional. The resistance is measured at the ends of the serpentine channel and can be used to determine the strain on the sensor. Additional channels can be added to
(Continued)

increase the sensitivity of the sensor. The sensors can be stacked on top of each other to increase the sensitivity of the sensor. In other embodiments, two sensors oriented in different directions can be stacked on top of each other and bonded together to form a bidirectional sensor. A third sensor formed by in the shape of a spiral or concentric rings can be stacked on top and used to sense contact or pressure, forming a three dimensional sensor. The three dimensional sensor can be incorporated into an artificial skin to provide advanced sensing.

8 Claims, 25 Drawing Sheets

Related U.S. Application Data

(60) Provisional application No. 61/538,841, filed on Sep. 24, 2011.

(51) Int. Cl.
```
G06F 3/01      (2006.01)
A61B 5/103     (2006.01)
A61B 5/11      (2006.01)
A61F 2/10      (2006.01)
A43B 13/20     (2006.01)
A43B 23/02     (2006.01)
A61B 5/00      (2006.01)
```

(52) U.S. Cl.
CPC ............ *A61B 5/1036* (2013.01); *A61B 5/112* (2013.01); *A61F 2/105* (2013.01); *B25J 13/08* (2013.01); *G01L 1/2287* (2013.01); *G06F 3/011* (2013.01); *G06F 3/014* (2013.01); *A61B 5/6807* (2013.01); *A61B 2562/0247* (2013.01); *A61B 2562/0261* (2013.01)

(58) Field of Classification Search
USPC .................................................. 73/862.627
See application file for complete search history.

(56) References Cited

U.S. PATENT DOCUMENTS

| | | | |
|---|---|---|---|
| 4,492,949 A | 1/1985 | Peterson et al. | |
| 4,547,668 A | 10/1985 | Tsikos | |
| 4,570,354 A | 2/1986 | Hindes | |
| 4,588,348 A | 5/1986 | Beni et al. | |
| 4,668,861 A | 5/1987 | White | |
| 4,682,608 A | 7/1987 | De Rigal et al. | |
| 5,086,785 A | 2/1992 | Gentile et al. | |
| 5,313,840 A | 5/1994 | Chen et al. | |
| 5,333,217 A | 7/1994 | Kossat | |
| 5,341,687 A | 8/1994 | Stan | |
| 5,442,729 A | 8/1995 | Kramer et al. | |
| 5,442,799 A | 8/1995 | Murakami et al. | |
| 5,553,500 A | 9/1996 | Grahn et al. | |
| 5,610,528 A | 3/1997 | Neely et al. | |
| 5,672,979 A | 9/1997 | Christopher | |
| 5,828,798 A | 10/1998 | Hopenfeld | |
| 5,886,615 A | 3/1999 | Burgess | |
| 5,917,165 A | 6/1999 | Platt et al. | |
| 5,959,863 A | 9/1999 | Hoyt et al. | |
| 6,050,962 A * | 4/2000 | Kramer ................ A61B 5/1071 |
| | | | 600/595 |
| 6,071,819 A | 6/2000 | Tai et al. | |
| 6,414,674 B1 | 7/2002 | Kamper et al. | |
| 6,825,539 B2 | 11/2004 | Tai et al. | |
| 6,915,701 B1 | 7/2005 | Tarler | |
| 6,951,143 B1 | 10/2005 | Adderton et al. | |
| 6,953,982 B1 | 10/2005 | Tai et al. | |
| 7,295,724 B2 | 11/2007 | Wang et al. | |
| 7,500,399 B2 | 3/2009 | Cheng et al. | |
| 7,658,119 B2 | 2/2010 | Loeb et al. | |
| 7,815,998 B2 | 10/2010 | Simpson et al. | |
| 7,854,173 B2 | 12/2010 | Cheng et al. | |
| 7,878,075 B2 | 2/2011 | Johansson et al. | |
| 8,033,189 B2 | 10/2011 | Hayakawa et al. | |
| 8,316,719 B2 | 11/2012 | Majidi et al. | |
| 2005/0160827 A1 | 7/2005 | Zdeblick et al. | |
| 2005/0261632 A1 | 11/2005 | Xu | |
| 2008/0087069 A1 | 4/2008 | Renken et al. | |
| 2008/0087105 A1 | 4/2008 | Renken et al. | |
| 2008/0108122 A1 | 5/2008 | Paul et al. | |
| 2009/0098521 A1 | 4/2009 | Kuo et al. | |
| 2009/0272201 A1 | 11/2009 | Loeb et al. | |
| 2010/0132476 A1* | 6/2010 | Cheng ................ G01B 7/18 |
| | | | 73/774 |
| 2011/0096327 A1 | 4/2011 | Papautsky et al. | |
| 2011/0132871 A1 | 6/2011 | White et al. | |
| 2011/0157088 A1 | 6/2011 | Motomura et al. | |
| 2011/0193363 A1 | 8/2011 | Nishiwaki | |
| 2013/0170218 A1 | 7/2013 | Wolk et al. | |
| 2013/0312541 A1 | 11/2013 | Majidi et al. | |
| 2014/0238153 A1 | 8/2014 | Wood et al. | |
| 2015/0088043 A1 | 3/2015 | Goldfield et al. | |

FOREIGN PATENT DOCUMENTS

| | | |
|---|---|---|
| JP | H03-088106 U | 9/1991 |
| JP | 3041795 U | 10/1997 |
| JP | H11-166804 A | 6/1999 |
| JP | 2006-258076 A | 9/2006 |
| JP | 2006-318175 A | 11/2006 |
| WO | 01/88935 A1 | 11/2001 |
| WO | 2007/089158 A1 | 8/2007 |
| WO | 2012/050938 A2 | 4/2012 |

OTHER PUBLICATIONS

Alirezaei et al., "A highly stretchable tactile distribution sensor for smooth surfaced humanoids", Humanoid Robots, 2007 7th IEEE-RAS International Conference on. IEEE 167-173 (2007).

Barlian et al., "Design and characterization of microfabricated piezoresistive floating element-based shear stress sensors", Sensors and Actuators A 134:77-87 (2007).

Cheng et al., "The development of a highly twistable tactile sensing array with stretchable helical electrodes", Sensors and Actuators A 166:226-233 (2011).

Chigusa et al., "Large Area Sensor Skin based on Two-Dimensional Signal Transmission Technology", Second Joint EuroHaptics Conference and Symposium on Haptic Interfaces for Virtual Environment and Teleoperator System (2007). (6 pages).

Cotton et al., "A Multifunctional Capacitive Sensor for Stretchable Electronic Skins", IEEE Sensors Journal 9 (12):2008-2009 (2009).

Dickey et al., "Eutectic Gallium-Indium (EGaIn): A Liquid Metal Alloy for the Formation of Stable Structures in Microchannels at Room Temperature", Advanced Functional Materials 18:1097-1104 (2008).

Duffy et al., "Rapid Prototyping of Microfluidic Systems in Poly(dimethylsiloxane)", Analytical Chemistry 70:4974-4984 (1998).

Herr et al., "New horizons for orthotic and prosthetic technology: artificial muscle for ambulation", Smart Structures and Materials 2004: Electroactive Polymer Actuators and Devices(EAPAD), Proceedings of SPIE 5385 (2004). (9 pages).

Hoshi et al., "Robot Skin Based on Touch-Area-Sensitive Tactile Element", Proceedings of the 2006 IEEE International Conference on Robotics and Automation 3463-3468 (2006).

Hsieh et al., "A Contact-Type Piezoresistive Micro-Shear Stress Sensor for Above-Knee Prosthesis Application", Journal of Microelectromechanical Systems 10(1):121-127 (2001).

Jiang et al., "A Flexible MEMS Technology and Its First Application to Shear Stress Sensor Skin", MEMS'97, Proceedings, IEEE., Tenth Annual International Workshop on. IEEE (1997). (6 pages).

Khang et al., "A Stretchable Form of Single-Crystal Silicon for High-Performance Electronics on Rubber Substrates", Science 311:208-212 (2006).

(56) References Cited

OTHER PUBLICATIONS

Kim et al., "Fabrication of microchannel containing nanopillar arrays using micromachined AAO (anodic aluminum oxide) mold", Microelectronic Engineering 84:1532-1535 (2007).
Kim et al., "A multiaxial stretchable interconnect using liquid-alloy-filled elastomeric microchannels", Applied Physics Letters 92:011904 (2008). (3 pages).
Kim et al., "Stretchable and Foldable Silicon Integrated Circuits", Science 320:507-511 (2008).
Kirchner et al., "Capacitive sensor for object ranging and material type identification", Sensors and Actuators A 148:96-104 (2008).
Kramer et al., "Wearable Tactile Keypad with Stretchable Artificial Skin", Robotics and Automation (ICRA), 2011 IEEE International Conference on. IEEE (2011). (5 pages).
Lacasse et al., "Characterization of the Electrical Resistance of Carbon-Black-Filled Silicone: Application to a Flexible and Stretchable Robot Skin", 2010 IEEE International Conference on Robotics and Automation, Achorage Convention District 4842-4848 (2010).
Lorussi et al., "Strain Sensing Fabric for Hand Posture and Gesture Monitoring", IEEE Transactions on Information Technology in Biomedicine 9(3):372-381 (2005).
Majidi et al., "A non-differential elastomer curvature sensor for softer-than-skin electronics", Smart Materials and Structures 20:105017 (2011). (7 pages).
Marculescu et al., "Electronic Textiles: A Platform for Pervasive Computing", Proceedings of the IEEE 91(12):1995-2018 (2003).
Menon et al., "Maskless lithography", Materials Today 26-33 (2005).
Pique et al., "Direct writing of electronic and sensor materials using a laser transfer technique", Journal of Materials Research 15(9):1872-1875 (2000).
Okamura et al., "Feature Detection for Haptic Exploration with Robotic Fingers", The International Journal of Robotics Research 20:925-938 (2001).
Park et al., "Exoskeletal Force-Sensing End-Effectors With Embedded Optical Fiber-Bragg-Grating Sensors", IEEE Transactions on Robotics 25(6):1319-1331 (2009).
Park et al., "Hyperelastic pressure sensing with a liquid-embedded elastomer", JJournal of Micromechanics and Microengineering 20:125029 (2010). (6 pages).
Park et al., "Design and Fabrication of Soft Artificial Skin Using Embedded Microchannels and Liquid Conductors", IEEE Sensors Journal 12(8):2711-2718 (2012).
Park et al., "Soft Artificial Skin with Multi-Modal Sensing Capability Using Embedded Liquid Conductors", Sensors, 2011 IEEE (2011). (4 pages).
Park et al., "Bio-inspired Active Soft Orthotic Device for Ankle Foot Pathologies", 2011 IEEE/RSJ International Conference on Intelligent Robots and Systems 4488-4495 (2011).
Puangmali et al., "State-of-the-Art in Force and Tactile Sensing for Minimally Invasive Surgery", IEEE Sensors Journal 8(4):371-381 (2008).
Quake et al., "From Micro- to Nanofabrication with Soft Materials", Science 290:1536-1540 (2000).
Rogers et al., "A curvy, stretchy future for electronics", Proceedings of the National Academy of Sciences 106(27):10875-10876 (2009).
So et al., "Reversibly Deformable and Mechanically Tunable Fluidic Antennas", Advanced Functional Materials 19:3632-3637 (2009).
Stirling et al., "Applicability of Shape Memory Alloy Wire for an Active, Soft Orthotic", Journal of Materials Engineering and Performance (2011). (5 pages).
Tajima et al., "Development of soft and distributed tactile sensors and the application to a humanoid robot", Advanced Robotics 16(4):381-397 (2002).
Takei et al., "Nanowire active-matrix circuitry for low-voltage macroscale artificial skin", Nature Materials 9:821-826 (2010).
Tseng et al., "A slow-adapting microfluidic-based tactile sensor", Journal of Micromechanics and Microengineering 19:085002 (2009). (8 pages).
Ulmen et al., "A Robust, Low-Cost and Low-Noise Artificial Skin for Human-Friendly Robots", 2010 IEEE International Conference on Robotics and Automation, Anchorage Convention District 4836-4841 (2010).
Unger et al., "Monolithic Microfabricated Valves and Pumps by Multilayer Soft Lithography", Science 288:113-116 (2000).
Ventrelli et al., "Development of a stretchable skin-like tactile sensor based on polymer composites", International Conference of Robotics and Biomimetics 123-128 (2009).
Vogt et al., "Multi-axis force sensing in a soft artificial skin", IEEE (2012).
Wettels et al., "Biomimetic Tactile Sensor Array", Advanced Robotics 22:829-849 (2008).
Whitney R., "The measurement of changes in human limb-volume by means of a mercury-in-rubber strain gauge", Proceedings of Physical Society 5P-6P (1949).
Xia et al., "Soft Lithography", Annual Review of Materials Science 28:153-184 (1998).
Xu et al., "IC-Integrated Flexible Shear-Stress Sensor Skin", Solid-State Sensor, Actuator and Microsystems Workshop 354-357 (2002).
Yamada et al., "Artificial Finger Skin having Ridges and Distributed Tactile Sensors used for Grasp Force Control", Proceedings of the 2001 IEEE/RSJ International Conference on Intelligent Robots and Systems 686-691 (2001).
Yoshikai et al., "Development of Soft Stretchable Knit Sensor for Humanoids' Whole-body Tactile Sensibility", 9th IEEE-RAS International Conference on Humanoid Robots 624-631 (2009).

\* cited by examiner

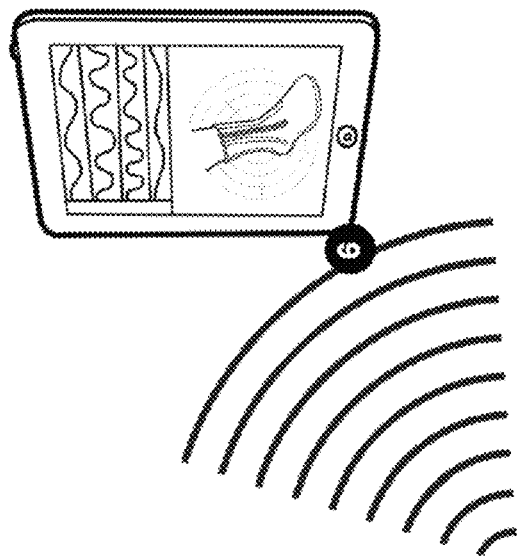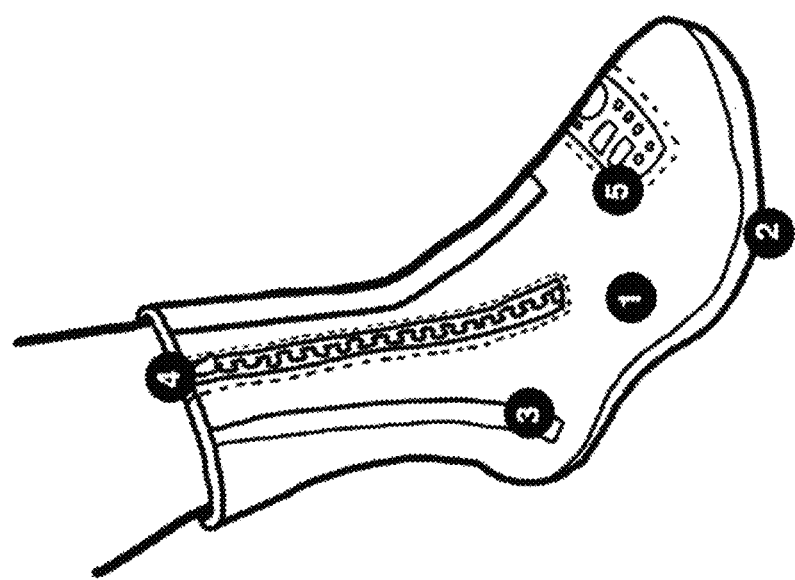
Figure 21

ARTIFICIAL SKIN AND ELASTIC STRAIN SENSOR

CROSS-REFERENCE TO RELATED APPLICATIONS

This application is a continuation of U.S. Ser. No. 14/346,853 filed Mar. 24, 2014, which is a 35 U.S.C. § 371 National Phase Entry Application of International Application No. PCT/US2012/056903 filed Sep. 24, 2012, which designates the U.S., and which claims any and all benefits under law including benefit under 35 U.S.C. § 119(e) of the U.S. Provisional Application No. 61/538,841, filed Sep. 24, 2011, the contents of each of which are incorporated herein by reference their entirety.

This application is related to U.S. Application Ser. No. 61/387,740, filed on Sep. 29, 2010, which is hereby incorporated by reference in its entirety.

GOVERNMENT SUPPORT

This invention was made with U.S. government support under grant No. CNS 0932015 awarded by the National Science Foundation. The U.S. government has certain rights in the invention.

REFERENCE TO MICROFICHE APPENDIX

Not Applicable

BACKGROUND

Technical Field of the Invention

The present invention is directed to elastic strain and pressure sensors and associated devices and systems for measuring motion and contact. Specifically, the present invention is directed to a hyper-elastic strain sensor that can be used to create an artificial skin that measure motion and touch.

Description of the Prior Art

Emerging technologies such as wearable computing [1] and soft active orthotics [2] will depend on stretchable sensors that register deformation and surface pressure. These softer-than-skin sensors must remain functional when stretched to several times their rest length, avoid hysteresis and permanent deformation, and preserve the natural mechanics of the wearer or host system. Hyper-elastic transducers for strain and pressure sensing represent just one aspect of the much broader and potentially revolutionary fields of elastically stretchable electronics and computing.

Current approaches to stretchable electronics include buckled (wavy) films of semiconductors for stretchable circuits and diodes [3-5] as well as elastomers that are embedded with microchannels of conductive liquid [6-8]. The latter approach utilizes many of the same molding, embossing and lithography techniques that are used to fabricate soft microfluidic devices [9-11]. One advantage of elastomers is their hyper-elasticity, which allows for mechanical durability and stretches as great as 1000%. Such properties are particularly favorable in wearable devices such as adaptive orthotics and insoles that must sustain large deformations and pressures.

Previous efforts in soft pressure and strain sensing and so called artificial skin include capacitive sensors composed of an elastic insulator layered between conductive fabric [12-14] or a silicone rubber sheet embedded with thin gold film [15]. Other efforts include resistive sensors composed of elastomer embedded with conductive microparticle filler [16-18] or ionic liquid [19-21] and a flexible artificial skin embedded with semiconductor nanowires [22].

Prior designs for pressure sensing are adapted from the Whitney strain gauge, which was introduced in 1949 to measure the change in circumferential girth of muscles and limbs [23, 24]. The original Whitney strain gauge was composed of a rubber tube filled with mercury and used a Wheatstone bridge to measure the change in electric resistance of the mercury channel corresponding to stretch. Recently, this principle has been extended to stretchable microelectronics, composed of eGaIn-filled microchannels embedded in polydimethylsiloxane (PDMS) rubber [6]. Embedded channels of eGaIn can also operate as a stretchable, mechanically tunable antenna [7] or as strain sensors [8] for measuring stretches of as much as 200%.

SUMMARY

The present invention is directed to a stretchable or elastic strain and/or pressure transducer composed of a flexible material embedded with conductive liquid in an array of microchannels. Pressing the surface or pulling the flexible elastomer material deforms the cross-section of the channels and changes the electric resistance of the conductive liquid in the microchannels.

The present invention is also directed to elastic sensors that respond to strain in a single direction. This can be accomplished by forming a set of elongated microchannels, each extending substantially parallel to a strain axis. The microchannels can be interconnected at their ends by loop portions to form a continuous channel over which to measure electrical resistance. In accordance with some embodiments of the invention, the loop portions can that have sufficient cross-sectional area in a direction transverse to the strain axis that strain in a direction transverse to the strain axis does not result in significant change in electrical resistance of the sensor, thus enabling unidirectional sensing. In these embodiments, the elastic sensors can be positioned to measure strain in one direction and multiple elastic sensors according to the invention can combined in different orientations to measure strain in two or more dimensions.

The present invention is also directed to elastic sensors that include embedded eGaIn channels that also operate as pressure sensors with 1 kPa resolution and 0-100 kPa range. In contrast to strain sensing, the mechanics of pressure sensing are complex and involve the use of elasticity and contact mechanics to derive a predictive mathematical model for describing the relationship between external pressure and electrical conductivity. In addition, the embedded microchannels can be produced using a maskless fabrication method that combines direct laser writing [25, 26] with soft lithography [9, 27] to produce micron-order feature sizes.

The present invention is directed to elastic sensors that can be formed in a compact package. The microchannels according to the invention can be closely spaced together in a horizontal plane as well as stacked vertically. This provides for highly sensitive sensor with a small, flexible, form factor. These sensor configurations can be fabricated in a skin that can be applied to robotic or orthopedic applications where joint position and motion sensing is needed.

These and other capabilities of the invention, along with the invention itself, will be more fully understood after a review of the following figures, detailed description, and claims.

BRIEF DESCRIPTION OF THE FIGURES

FIG. 18 shows a two-dimensional, plane strain representation of elastomer embedded with a microchannel of width w and height h according to an embodiment of the invention. The surface of the elastomer is subject to a pressure p uniformly distributed over a width a.

FIG. 21 shows a system for measuring forces and motion of the foot according to one embodiment of the invention.

DETAILED DESCRIPTION OF PREFERRED EMBODIMENTS

The present invention is directed to elastic sensors and methods for fabricating elastic sensors that respond to strain in a single direction. This can be accomplished by forming a set of elongated microchannels in an elastic material such as silicone rubber sheet (EcoFlex 0030, SmoothOn, Easton, Pa.; PDMS, Dow Corning). Each microchannel can be formed to extend substantially parallel to a strain axis and the microchannels can be interconnected at their ends by loop portions to form a continuous channel over which to measure electrical resistance. The continuous channel can be filled with a conductive material, such as a conductive liquid, for example, non-toxic eutectic gallium-indium (eGaIn, BASF). In accordance with some embodiments of the invention, the loop portions can that have sufficient cross-sectional area in a direction transverse to the strain axis that strain in a direction transverse to the strain axis does not result in significant change in electrical resistance of the sensor and enables unidirectional sensing. In these embodiments, the elastic sensors can be positioned to measure strain in one direction and multiple elastic sensors according to the invention can combined in different orientations to measure strain in two or more dimensions.

Figures 1, 2:
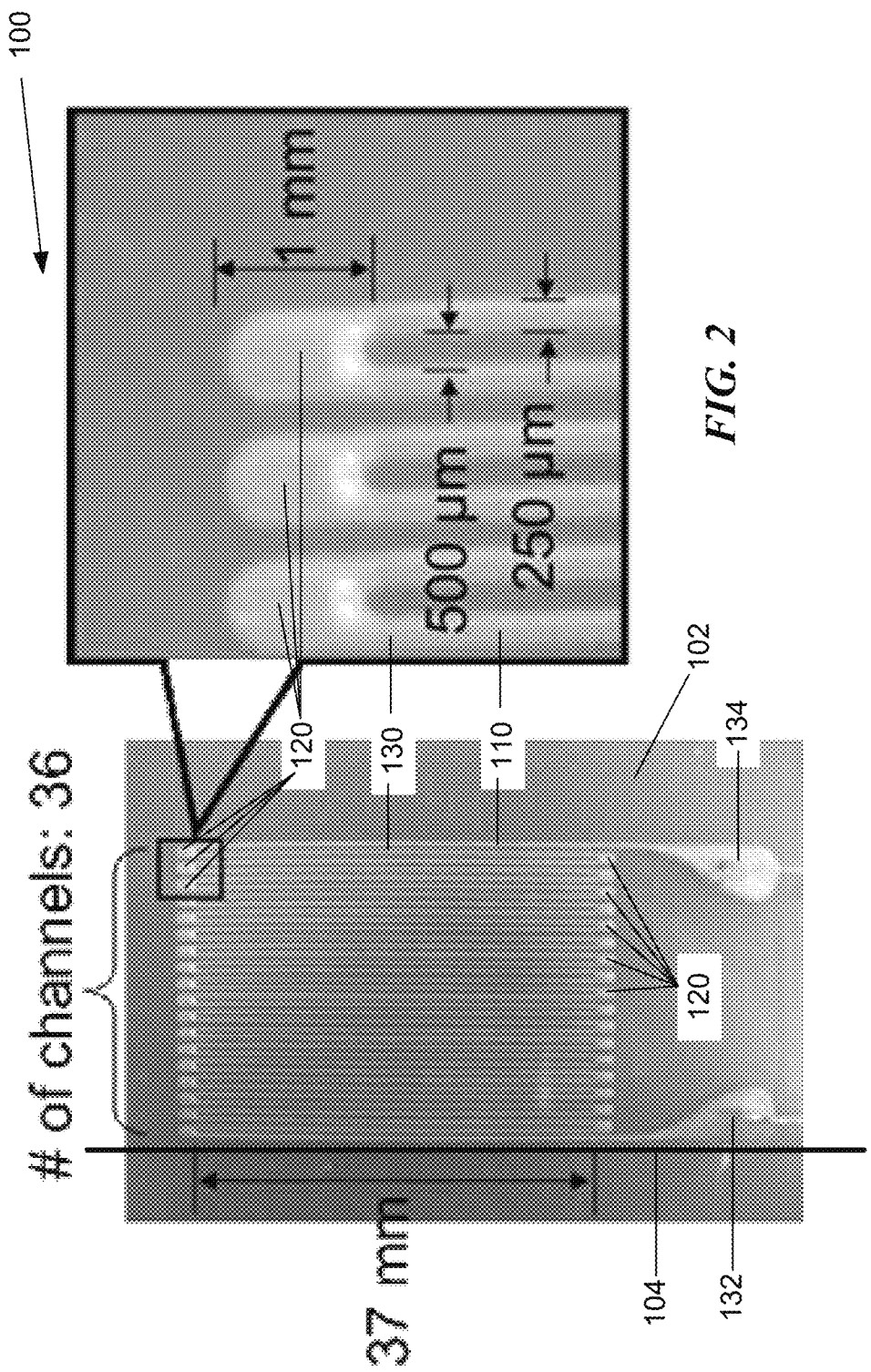
FIG. 1 shows an elastic strain sensor according to an embodiment of the invention.
FIG. 2 shows a close-up view of the loop portions of an elastic strain sensor according to the embodiment of the invention shown in FIG. 1.

FIG. 1 and FIG. 2 show an elastic strain sensor 100 according to an embodiment of the present invention. The strain sensor 100 can be formed from a flexible elastic substrate material 102 by molding or etching to form elongated microchannels 110 and loop portions 120. The microchannels 110 and the loop portions 120 can be filled with a conductive liquid 130 and the strain on the sensor 120 can be determined from changes in the electrical resistance of the conductive liquid 130 as the elastic material and the conducting liquid are stretched. The loop portions 120 connect adjacent ends of the elongated microchannels 110 to form a serpentine channel that extends from a first connection reservoir 132 to a second connection reservoir 134. The first connection reservoir 132 and the second connection reservoir 134 can be used to inject the conductive liquid 130 so that it flows through each of the micro channels 110 and can receive wires to connect to the control system that measure the electrical resistance of the full extent of the combined microchannels 110 and loop portions 120.

FIG. 2 shows an enlarged view of the loop portions 120 of the strain sensor 100. The loop portions 120 can be substantially larger than the microchannels 110 in the transverse direction, so that strain applied in a direction transverse to the strain axis 104 does not result in appreciable increase in electrical resistance. In this way, the elastic strain sensor 100 can be sensitive to strain applied along the strain axis 104 or strain having a component that extends along the strain axis 104 and insensitive to strain transverse to the strain axis 104.

Each of the microchannels 110 can be formed with a uniform cross-section and filled with the conducting liquid, such as eutectic gallium-indium (eGaIn) available from BASF, Florham Park, N.J. Each of the microchannels 110 can be substantially straight, zig-zag, or S shaped. In accordance with one embodiment, the microchannels 110 can be connected end to end by the loop portions 120 such that a single continuous channel filled with the conducting liquid 130 can be formed. In this embodiment, each microchannel extends parallel to the strain axis and when the elastic material is subject to strain, each of the microchannels, along with the conductive liquid 130 carried therein, can become elongated increasing the electrical resistance. One advantage of the present invention is that each microchannel becomes elongated causing the overall length of the channel of conducting liquid to be elongated in per portion to the number of microchannels. Adding microchannels can be used to increase the sensitivity of the strain sensor. In some embodiments, the sensor can include 36 or more microchannels 110, and each microchannel 110 can be 250 µm wide by 250 µm high and the loop portions can be 1.0 mm wide by 250 µm high.

Each of the microchannels 110 can be connected by loop portions 120 that forms a continuous channel that serpentines over a surface. In accordance with some embodiments of the invention, the loop portions 120 can be substantially larger in cross-sectional area than the unstrained microchannels 110 such that strain in a direction transverse to the strain axis 104 does not cause significant change in electrical resistance. In this embodiment, the elastic stain sensor 100 becomes unidirectional along the strain axis 104.

The elastic strain sensor 100 can be formed from any elastic material including silicone and rubber materials (e.g., EcoFlex0030 and EcoFlex0050, SmoothOn, Easton, Pa.; PDMS, Dow Corning, Midland, Mich.; P-20 and GI-1120, Innovative Polymers, Saint Johns, Mich.; Tap Platinum Silicone System, Tap Plastics, CA) and soft polyurethane materials (e.g., Dragon Skin, SmoothOn, Easton, Pa.; IE-35A, Innovative Polymers, Saint Johns, Mich.). In accordance with one embodiment, a low viscosity (3000 cps) mixture of EcoFlex can be used to reproduce the fine features of the mold.

In general, the process for fabricating the sensor can include mold making, casting the layer(s), bonding the layers together and injecting the conducting liquid. In accordance with one embodiment of the invention, the elastic strain sensor 100 can be produced by casting the silicone material into one or more 3D printed molds (e.g., Connex 500, Objet Geometries Ltd.). In this embodiment, one layer can be patterned to form the microchannels 110, loop portions 120 and connection reservoirs 132, 134 and the other layer is not patterned, providing an essentially flat layer to be bonded to the patterned layer. After curing under ambient conditions for approximately 4 h, the elastomer layers can be removed from the molds and bonded together with a thin, uncured layer of the elastomer material (e.g., EcoFlex).

To avoid filling the exposed microchannels, the unpatterned elastomer mold can be first spin-coated with a thin, uncured layer (e.g., 1100 rpm for 45 s) of elastomer, which can be then partially cured, for example, for 30 s at 60° C. in a convection oven. The patterned elastomer mold can then be gently bonded to the unpatterned surface. The two elastomer layers (the unpatterned smooth sheet and the patterned sheet containing the exposed microchannels) can be cured together under ambient conditions for several hours. After the sheets are sufficiently bonded together, a syringe can be used to fill each channel with eGaIn. Lastly, the ends of the channel can be sealed with a final coating of uncured elastomer material.

In accordance with another embodiment of the invention, sensors with microchannels in the 20-300 micrometer range can be fabricated by casting an elastomer material (e.g., PDMS) in an SU-8 mold that is patterned by maskless soft lithography. Photoresist (SU-8 2050) can be spun onto a clean silicon wafer, for example, at 500 rpm for 10 s (spread), followed by 4000 rpm for 30 s (spin). The wafer can then be placed on a hot plate at 65° C. for 3 min and 95° C. for 6 min. Next, the coated wafer can be patterned via direct-write laser exposure [25, 26] using a diode pumped solid-state (DPSS) 355 nm laser micromachining system. The system can be calibrated to expose a 20 µm thick SU-8 coating to produce channels with a range of 25 to 1000 µm in width and ≥50 µm spacing. The wafer can be post-baked on a hot plate, for example, at 65° C. for 1 min and 95° C. for 6 min, and consequently developed for 5 min in SU-8 developer. In order to allow for easier removal in subsequent molding steps, a hydrophobic monolayer can be introduced through vapor deposition. The patterned wafer can be placed in an evacuated chamber (20 mTorr) with an open vessel containing a few drops of trichloro (1H,1H,2H,2H-perfluorooctyl) silane (Aldrich) for 3 h. Next, the PDMS (Sylgard 184; Dow Corning, Midland, Mich.) can be cast in liquid form (e.g., 10:1 mass ratio of elastomer base to curing agent) against the silicon wafer. PDMS can then be partially cross-linked in the mold by oven-curing at 60° C. for 30-40 min. The microchannels can be constructed by bonding patterned PDMS to unpatterned PDMS via oxygen plasma treatment (Technics Plasma Stripper/Cleaner; 60 W for 30 s). The sealed microchannels can be completely cured, for example, at 60° C. overnight. Finally, the microchannels can be filled with eGaIn using conventional tubing and syringe dispensing.

Additional layers with patterned elastomer (e.g., PDMS) can be formed by molding the patterned layer with an unpatterned back surface. The unpatterned back surface can similarly be bonded to an additional patterned layer. In some embodiments, the microchannels for each layer can be aligned with a common axis and connected by holes or openings in the patterned layer(s) that provides an interconnect between layers. In some embodiments, the microchannels for each layer can be isolated so as to provide more than one sensor. In some embodiments, the microchannels for each layer can extend along intersecting axes to allow strain sensing in multiple directions.

Figure 3:
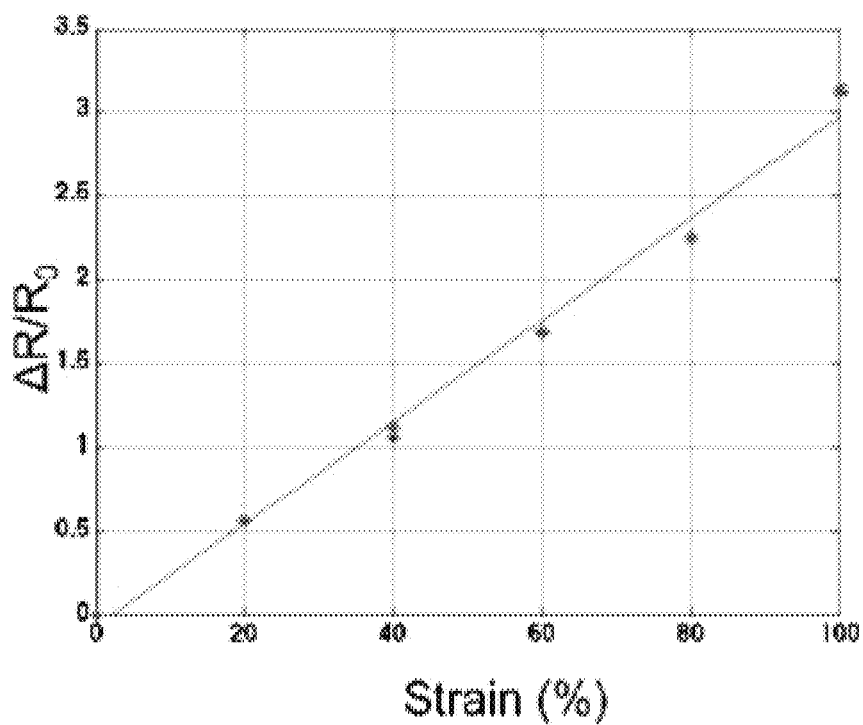
FIG. 3 shows the calibration plot of an elastic strain sensor according to an embodiment of the invention.

In accordance with one embodiment of the invention, a strain sensor was formed with 36 channels, each channel being 250 µm wide by 250 µm high and the loop portions being 1.0 mm wide by 250 µm high. This device had a nominal resistance at rest of 5.8 ohms. The gauge factor of the strain gauge can be determined:

$$\frac{\Delta R}{R_0} = G\varepsilon + \alpha\theta \quad (1)$$

Where $\Delta R$ is the resistance change, R is the resistance at rest, $\varepsilon$ is the strain, $\alpha$ is the temperature coefficient and $\theta$ is the temperature change. Assuming there is no temperature effect, the gauge factor was determined empirically to be 3.04. FIG. 3 shows that the plot of the change in resistance and the strain is substantially linear without considering temperature effects.

Figure 4:
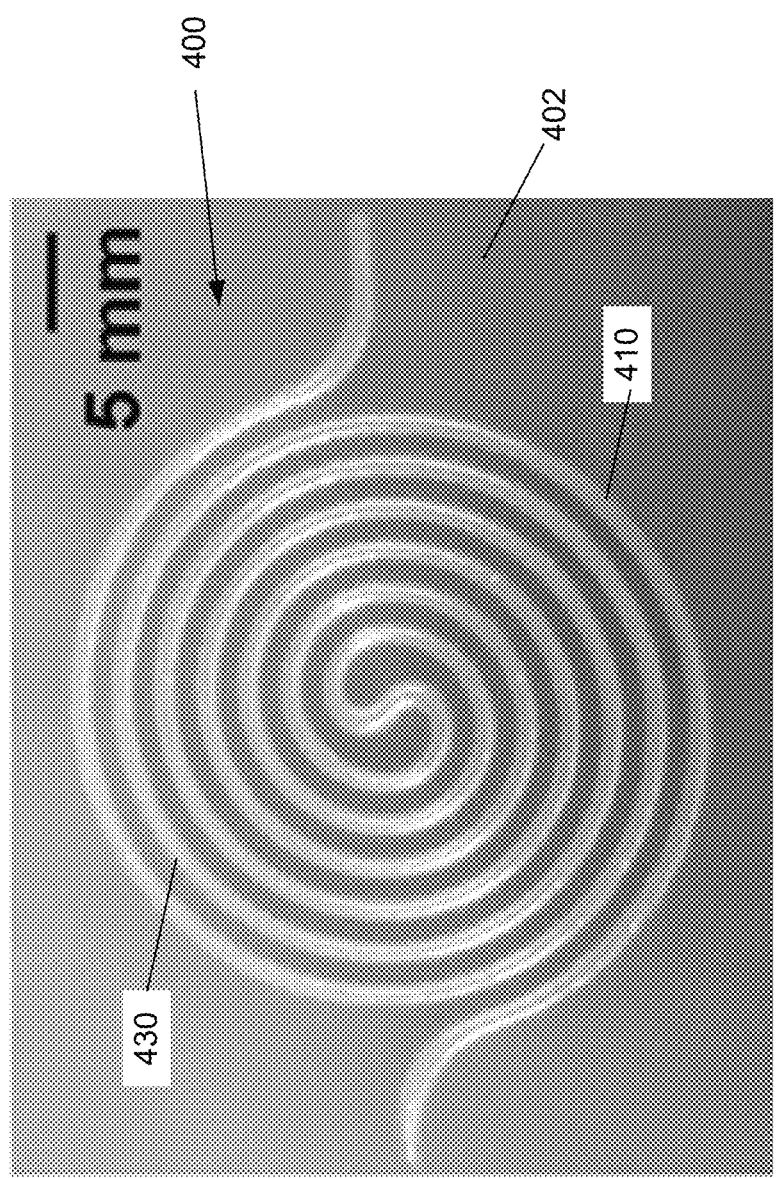
FIG. 4 shows an elastic pressure sensor according to an embodiment of the invention.

FIG. 4 shows a pressure sensor 400 according to an embodiment of the present invention. In this embodiment, the pressure sensor 400 can be formed from a flexible elastic substrate material 402 by molding or etching to include a circular microchannel 410 formed in a spiral or set of concentric loops. The circular microchannel 410 can be filled with a conductive liquid 430 and the pressure on the sensor 400 can be determined from changes in the resistance of the conductive liquid 430 as the elastic material and the conductive liquid is compressed.

In accordance with one embodiment of the invention, a straight microchannel filled with eGaIn material can be used for simultaneously measuring applied pressure and electrical resistance. The ends of the eGaIn-filled channels can be wired to a precision multimeter (Fluke 8845A). A rigid glass rectangle of width a and length L can be pressed into the sensor with a digital height gauge (Swiss Precision Instruments, Inc.). In order to distribute the pressure more uniformly and better simulate tactile or elastic contact, a 5 mm thick sheet of elastomer with the same area as that of the glass rectangle can be inserted between the glass and the sensor surfaces. The sensor can be supported by an electronic scale (6000 g OHAUS Scout Pro) that measures the total force F exerted on the surface. The average pressure exerted over the area of contact can be calculated as p=F/aL.

The change in electrical resistance $\Delta R$ of the embedded, conductive liquid-filled channels can be determined empirically as a function of the applied pressure p using an experimental setup. Both experimentally measured values (open circles) and theoretical predictions (solid curve) are plotted in FIG. 16 for an elastomer containing a straight channel with width w=2 mm, height h=1 mm, and with a top face that is at a distance z=2 mm from the surface of the elastomer. Pressure is applied over an area of length L=27 mm and width a=25 mm. For this set of measurements, the major axis of the contact area (which has length L) can be aligned with the centerline of the channel. The plot contains data points from multiple loading and unloading cycles, demonstrating significant repeatability and low hysteresis.

Figure 16:
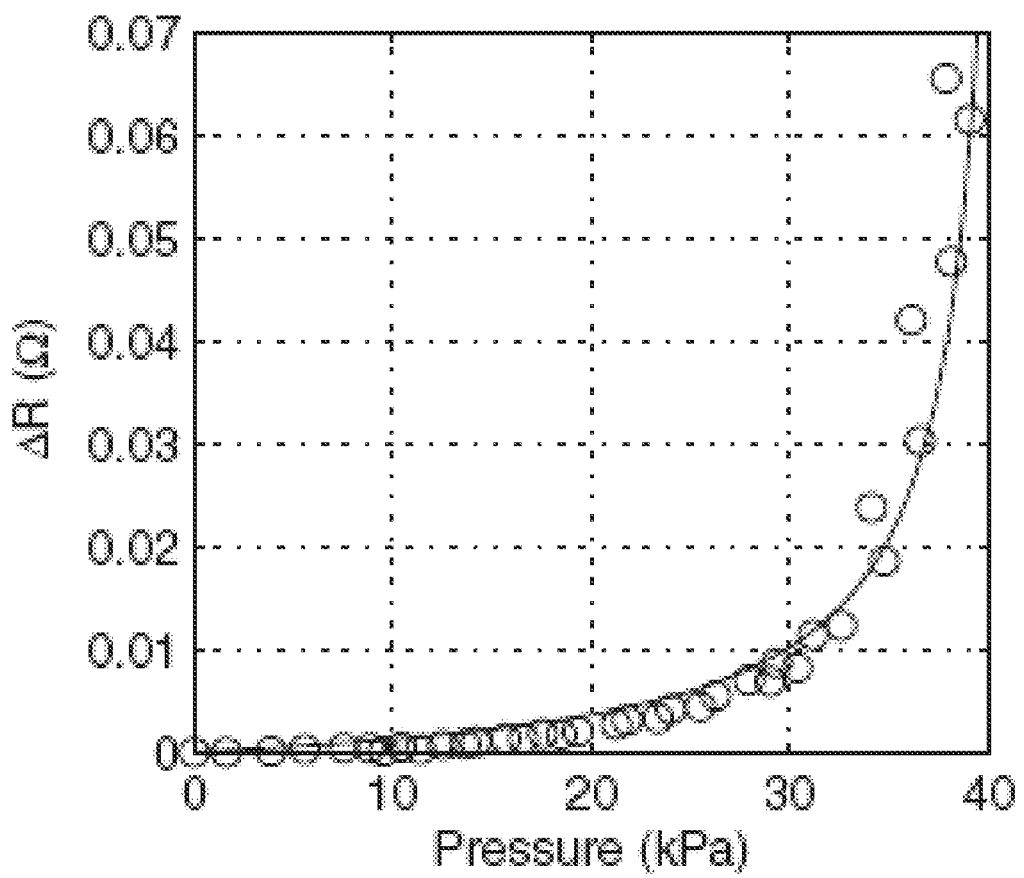
FIG. 16 shows a plot of the change in electrical resistance as a function of applied pressure according to an embodiment of the invention.

As shown in the plot in FIG. 16, the change in electrical resistance $\Delta R$ increases exponentially with applied pressure. This curve closely matches the theoretical prediction, which is represented by the solid line. It is important to note that no data fitting is used; the theoretical curve is derived entirely from the prescribed geometry, the prescribed pressure, the known resistivity $\rho$=29.4×10−8 $\Omega$m−1 of eGaIn [6] and the elastic modulus E=125 kPa of the rubber, which are independently measured by comparing the pressure with the depth of indentation. The closed-form theoretical solution and derivation are presented in the next section.

Figure 17:
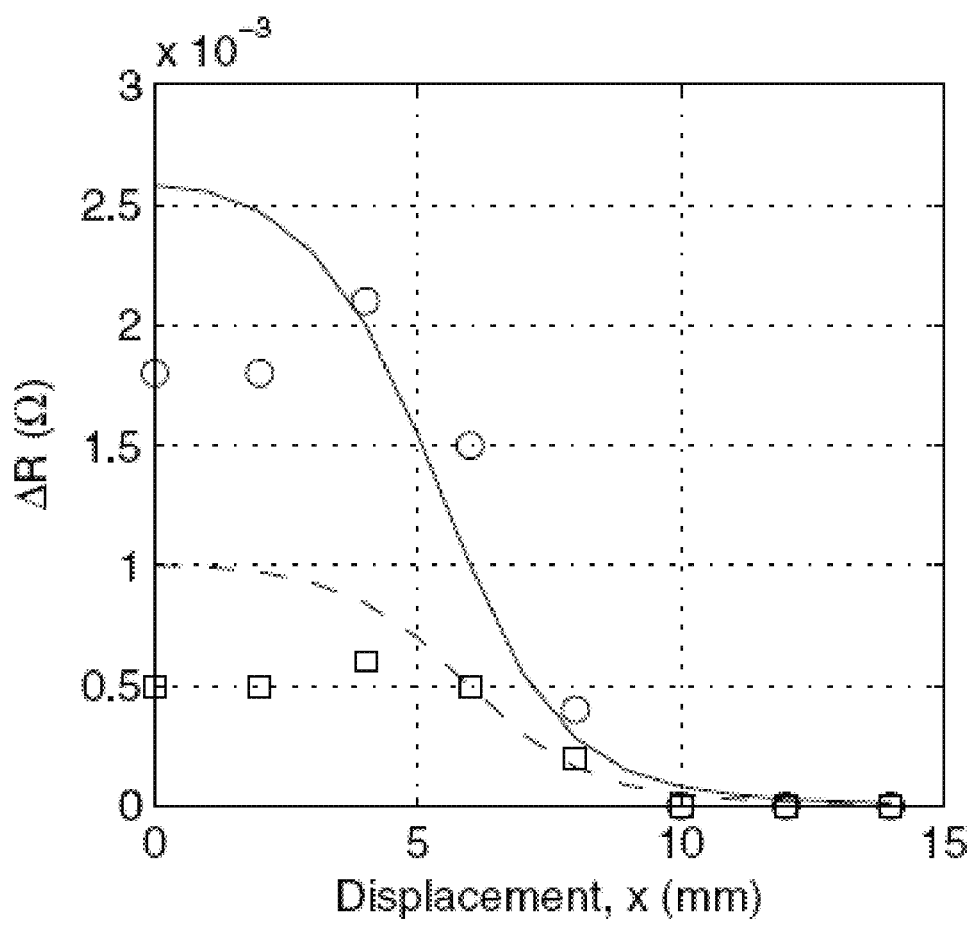
FIG. 17 shows a plot of the change in electrical resistance as a function of lateral displacement (x) according to an embodiment of the invention.
Figure 18:
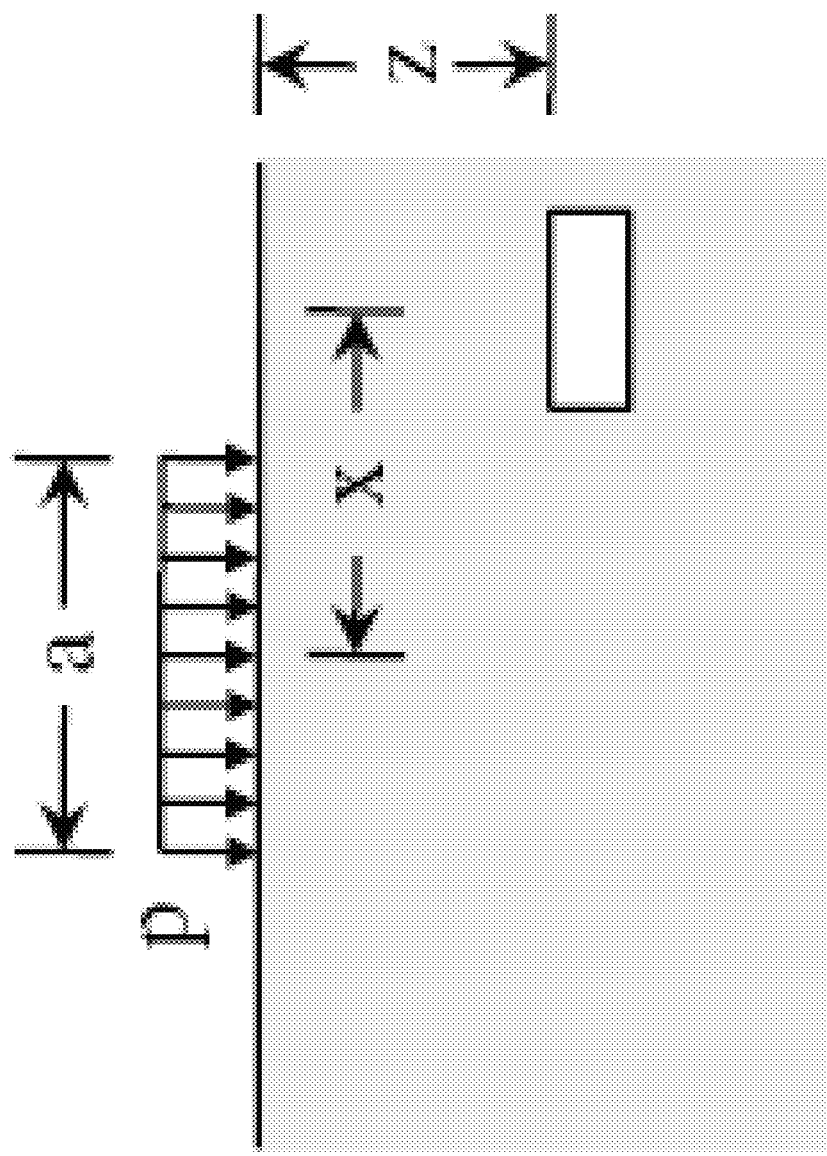

As expected, $\Delta R$ decreases the further the center of applied pressure moves from the channel. FIG. 17 presents a plot of $\Delta R$ versus lateral displacement x for pressures p=15 kPa and p=25 kPa. As illustrated in FIG. 18, x is defined as the horizontal distance between the channel centerline and the major axis of the contact area. For both pressures, the signal $\Delta R$ decreases significantly with increasing relative displacement. The theoretical predictions, which are represented by dashed and solid curves for 15 and 25 kPa, respectively, are reasonably consistent with experimental measurements, which do correspond to the open squares and circles. While the surface pressure is approximately uniform, there are small stress concentrations near the edges of the contact zone. Hence, when x=4 mm and the channel is between the center and the edge of the contact zone, the nominal stress is slightly greater and a larger response $\Delta R$ is measured. Lastly, a plot of $\Delta R$ versus channel depth z (for x=0) is presented in FIG. 6. Referring to FIGS. 5A-5H, z is defined as the distance between the surface of the elastomer and the top wall of the channel. As demonstrated in the experimental results, the resistance change $\Delta R$ decreases the farther the channel is from the surface. This trend is also predicted by the theory, although the theory appears to overestimate the absolute change by as much as a factor of 2.

The mechanics of the microchannel embedded elastomer are complex and in accordance with one embodiment of the invention, can be modeled with an approximate mathematical analysis. In accordance with this embodiment, a two-dimensional representation of a straight channel with rectangular cross-section embedded in an elastomeric halfspace can be used to approximate the microchannel. As illustrated in FIG. 18, the channel has width w, height h, and a top wall that is at a distance z from the surface of the elastomer.

A uniform external pressure p can be applied to the surface of the elastomer over an area of width a. As shown in FIG. 18, the centers of the channel and the area of applied pressure are offset horizontally by a distance x. For channels close to the center of the applied pressure (i.e. |x|<a/2 and z<a), elastic deformation will reduce the cross-sectional area and hence increase electric resistance. The reduction in cross-sectional area is primarily governed by the magnitude of the vertical component of the stress tensor: $\sigma_z=\sigma_z(x, z; p, a)$. Since the applied pressure is compressive, $\sigma_z$ will have a negative sign. As in the case of crack growth in linear elastic fracture mechanics (LEFM), the field lines of the internal stress $\sigma_z$ will concentrate about the edges of the microchannel [28, 29]. This is in order to satisfy the boundary condition of zero traction on the walls of the channel. Because the channel is filled with fluid, the walls will not be traction free but are instead subject to hydrostatic pressure. However, this internal channel pressure is considered negligible in comparison to the induced nominal stress $\sigma_z$ and so zero traction is assumed.

According to LEFM, an average vertical stress $\sigma_z$ applied in the vicinity of a crack will increase the gap between the crack faces by an amount $\Delta h=2(1-v^2)w\sigma_z/E$, where v is Poisson ratio and E is the elastic modulus [28]. Because the microchannels are small compared to the dimensions of the elastomer, their influence on the stress distribution will be negligible except in the immediate vicinity of each channel. Therefore, for channels below the area of contact (|x|<a/2 and z<a), the average stress in the neighborhood of the channel may be approximated as $\sigma_z=-p$. Substituting this into the expression for $\Delta h$ implies that the total change in electrical resistance will be approximately $$\Delta R=\rho L/wh\{(1/(1-2(1-v2)wp/Eh))-1\} \quad (2)$$

In general, p should be replaced with $\chi p$, where $\chi=\chi(x, z)$ is a correction that depends on the relative position (x, z) of the channel centerline. The correction $\chi=-\sigma_z/p$ can be obtained by solving $\sigma_z$ using Boussinesq's method: [30]

$$\sigma_z = \int_{-a/2}^{a/2}\int_{-\infty}^{\infty} -\frac{3pz^3}{2\pi}\{(x-X)^2+Y^2+z^2\}dYdX \quad (3)$$

A closed-form, elementary expression for $\sigma_z$ can be obtained with Maple 13 (Waterloo Maple Incorporated, 2009). Solving for $\chi$ yields $$\chi=(c_1 c_2-c_3)/c_4 \quad (4)$$

where $c_1=\tan^{-1}((a+2x)/2z)+\tan^{-1}((a-2x)/2z)$ $c_2=-8x^2a^2+32x^2z^2+8z^2a^2+16x^4+16z^4+a^4$ $c_3=-16zax^2+4za^3+16z^3a$ $c_4=\pi(4x^2\ 4xa+a^2+4z^2)(4x^2-4xa+a^2+4z^2)$.

This is used to evaluate the change in electrical resistance as a function of x and z:

$$\Delta R = \frac{\rho L}{wh}\left\{\frac{1}{1-2(1-v^2)w\chi p/Eh}-1\right\} \quad (5)$$

Figure 19:
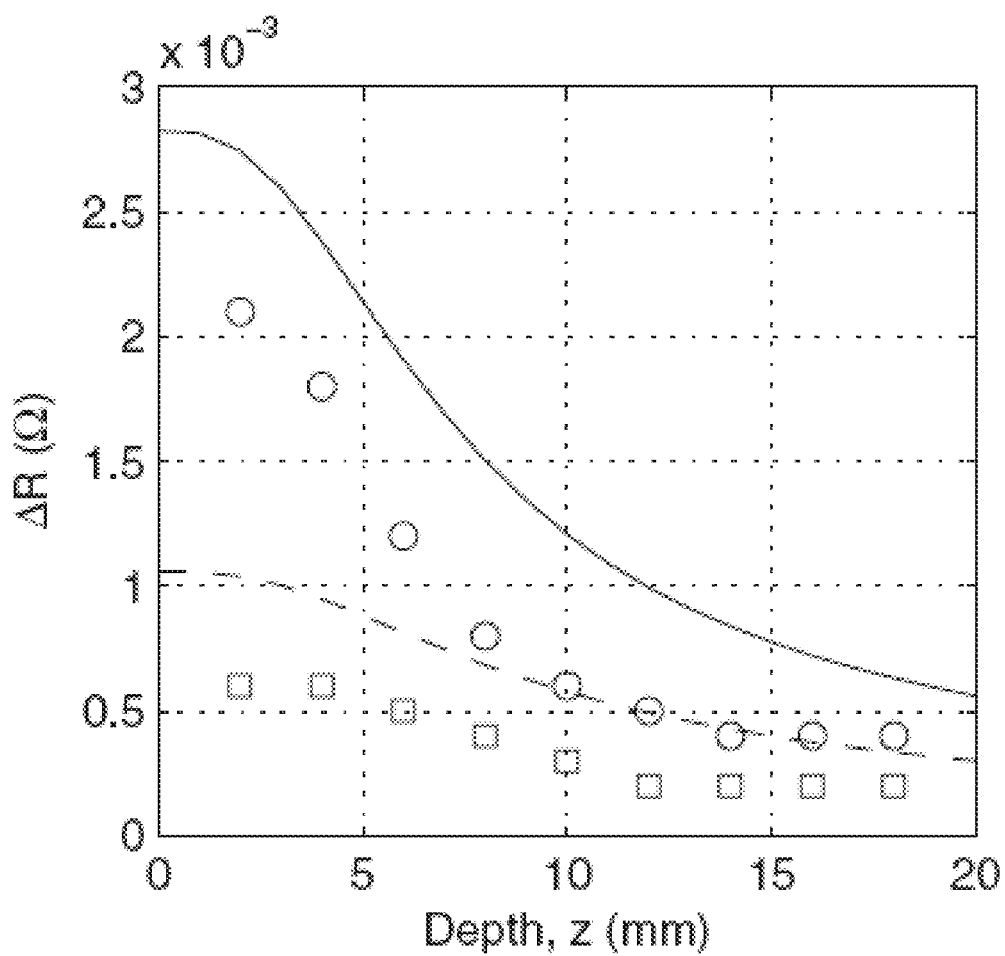
FIG. 19 shows a plot of the change in electrical as a function of depth z of the sensor according to an embodiment of the present invention.

In accordance with some embodiments of the invention, the derived relations are consistent with experimental measurements for a wide range of pressures p and relative positions (x, z). In FIG. 17 and FIG. 19 there appears to be close to a 50% discrepancy between the theory and the experiment. This could be due to the simplifying assumptions of the theoretical model, which is based on plane strain linear elasticity, ignores the influence of the channel on global stress distribution, and assumes uniform channel collapse with zero surface traction and constant width. Relaxing these assumptions can be used determine a more accurate set of equations that better match the experimental result. However, these models require numerical computations or finite element analyses that will not yield an algebraic closed-form solution, such as the one presented in equation (5).

In addition to capturing the principal mechanics of the elastomer pressure transducer, the theory reveals several properties that can be exploited for customized functionality. The first property allows for mechanical decoupling between pressure sensing and stretch sensing. Thus, a system according to embodiments of the invention can be able to distinguish whether change in microchannel conductivity is induced by pressure or stretching.

The second property relates to the sensor bandwidth, i.e. the range of pressures that the sensor can detect. Sensor response to pressure and stretch are decoupled by selecting the appropriate microchannel depth z and path (e.g. straight, serpentine and spiral). As demonstrated in FIG. 19, the sensor response vanishes as z exceeds the width a of the contact area. In contrast, the change in electrical resistance due to channel elongation is invariant with microchannel depth. Instead, elongation response is governed by the simple formula $\Delta R/R0=\lambda^2-1$, where $R0=\rho L/wh$ is the original resistance of the unstretched channel and the stretch $\lambda=L_f/L$ is the ratio of the stretched length $L_f$ to the natural length L. This implies that a microchannel embedded deep within the elastomer (a distance z>a from the surface for anticipated values of a) will only measure stretch and not pressure.

Alternatively, a spiral-shaped microchannel embedded close to the elastomer surface, as shown in FIG. 1(a), will detect pressure but not uniaxial stretching. This is because increased electrical resistance in one direction is balanced by reduced resistance in the perpendicular direction.

Sensor bandwidth is controlled by a characteristic pressure $\hat{p}=Eh/w$ and thus depends only on the elastic modulus E of the elastomer and the aspect ratio h/w of the microchannel cross-section. Noting that $R_0=\rho L/wh$ is the natural resistance of the channel, it follows from equation (2) that for a channel embedded near the surface of the elastomer, $\Delta R/R_0=1/(1-2(1-v^2)p/\hat{p})$. Depending on the ratio $p/\hat{p}$, the relative change in electrical resistance can range from fractions of a percent to orders of magnitude. Consider, for example, EcoFlex (E=125 kPa) embedded with a microchannel of width w=100 µm and thickness h=20 µm. In response to a typical keystroke pressure in the range of 1-10 kPa, the electrical resistance of the embedded microchannel would change by an order of 1%. In contrast, peak pressure in foot-ground contact during walking is in the order of 100 kPa, which would result in an approximately 50% change in electrical resistance. For all applications, the design parameters E and h/w should be selected such that the characteristic pressure $\hat{p}$ is comparable to the range of anticipated pressures p.

Figure 5:
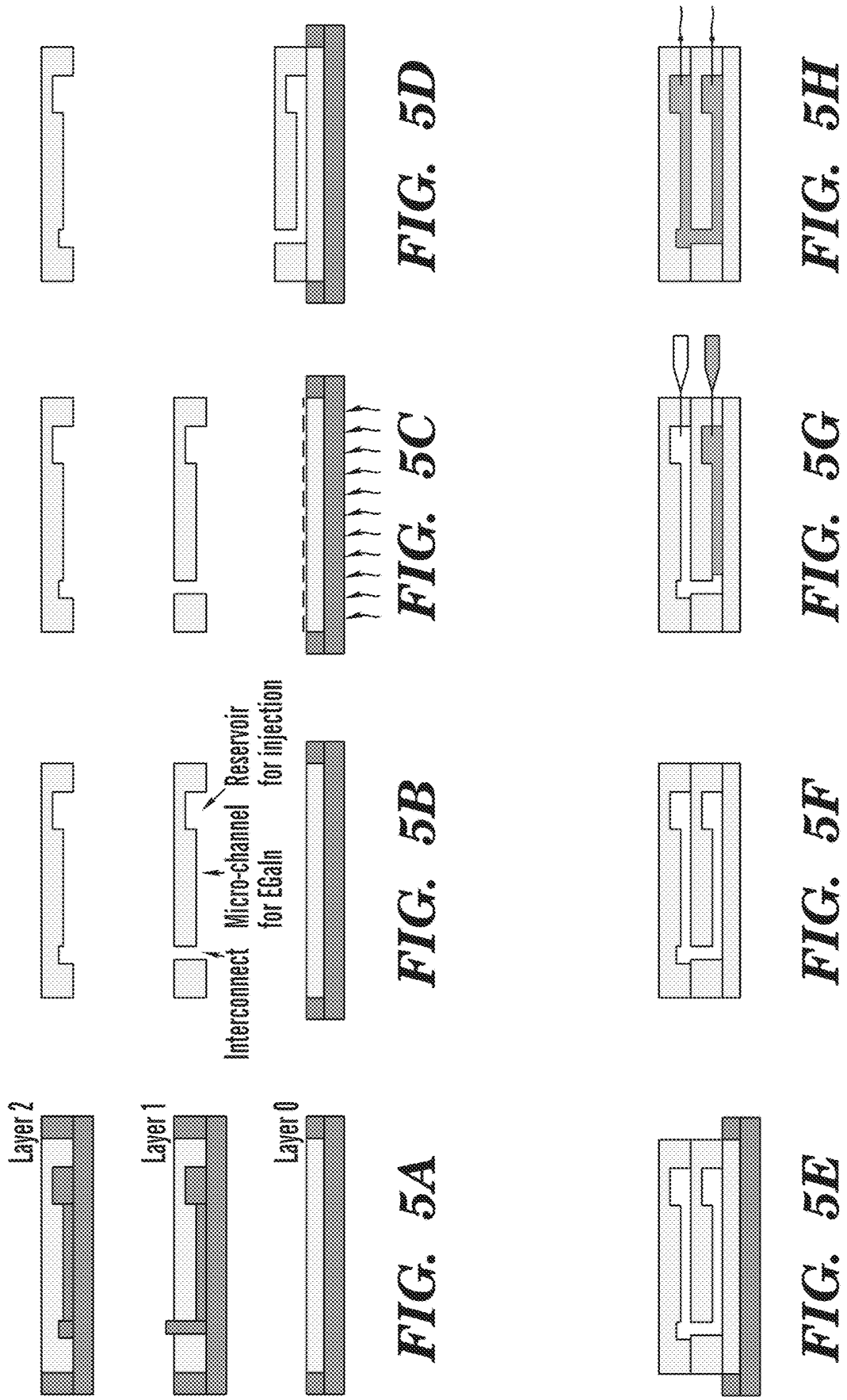
FIG. 5A, FIG. 5B, FIG. 5C, FIG. 5D, FIG. 5E, FIG. 5F, FIG. 5G, and FIG. 5H show a method of fabricating an elastic strain sensor according to an embodiment of the invention.

FIGS. 5A-5H show a diagram of a method of fabricating a multi-layer strain sensor according to an embodiment of the invention. The method includes preparing the molds for each layer. In this embodiment, two layers of sensors are provided, so three molds can be used to form three layers of elastomer material as shown in FIG. 5A. After the elastomer material cures, the cast material is removed from the molds. As shown in FIG. 5B, layer 0 is the unpatterned layer and can remain in the mold and Layer 1 can include an interconnect to connect the microchannels formed between the layers of elastomer material. Layer 0 can be spin coated with the elastomer material at 2000 rpm for 50 sec. and then partially cured at 60 degrees C. for 1 min, as shown in FIG. 5C. Layer 1 can be bonded to Layer 0 by laminating with a light pressure as shown in FIG. 5D. Layer 2 can be bonded to the top surface of Layer 1 by the same process as Layer 1 was bonded to Layer 0. The top surface of Layer 1 can be spin coated with the elastomer material and then partially cured, as shown in FIG. 5E. Additional layers of elastomer material can be bonded using the same process. After the last layer is bonded to the elastic strain sensor, Layer 0 can be removed from the mold, as shown in FIG. 5F. The conducting liquid 130 can be injected into the channels 110 using a syringe. In one embodiment of the invention, more than one syringe can be used during the injecting process. At least one syringe can be used to inject the conducting liquid, such as eGaIn into one connection reservoir while at least one other syringe can be used to remove the rapped air, such as from the other connection reservoir, as shown in FIG. 5G. After the conducting liquid has filled the channels, the loop portions and the connection reservoirs, wires can be inserted into the connection reservoirs, shown in FIG. 5H. The wire can be used to electrically connect the elastic strain sensor to the input electronics that will read the sensor output.

In addition to the sensors shown in FIG. 1 and FIG. 2, the pressure sensors shown in FIG. 4 can also be fabricated using layers as shown in FIGS. 5A-5H. In this embodiment, the circular pattern of the pressure sensor can be formed in Layer 1 and bonded to an unpatterned layer, Layer 0 as described herein.

Figure 6:
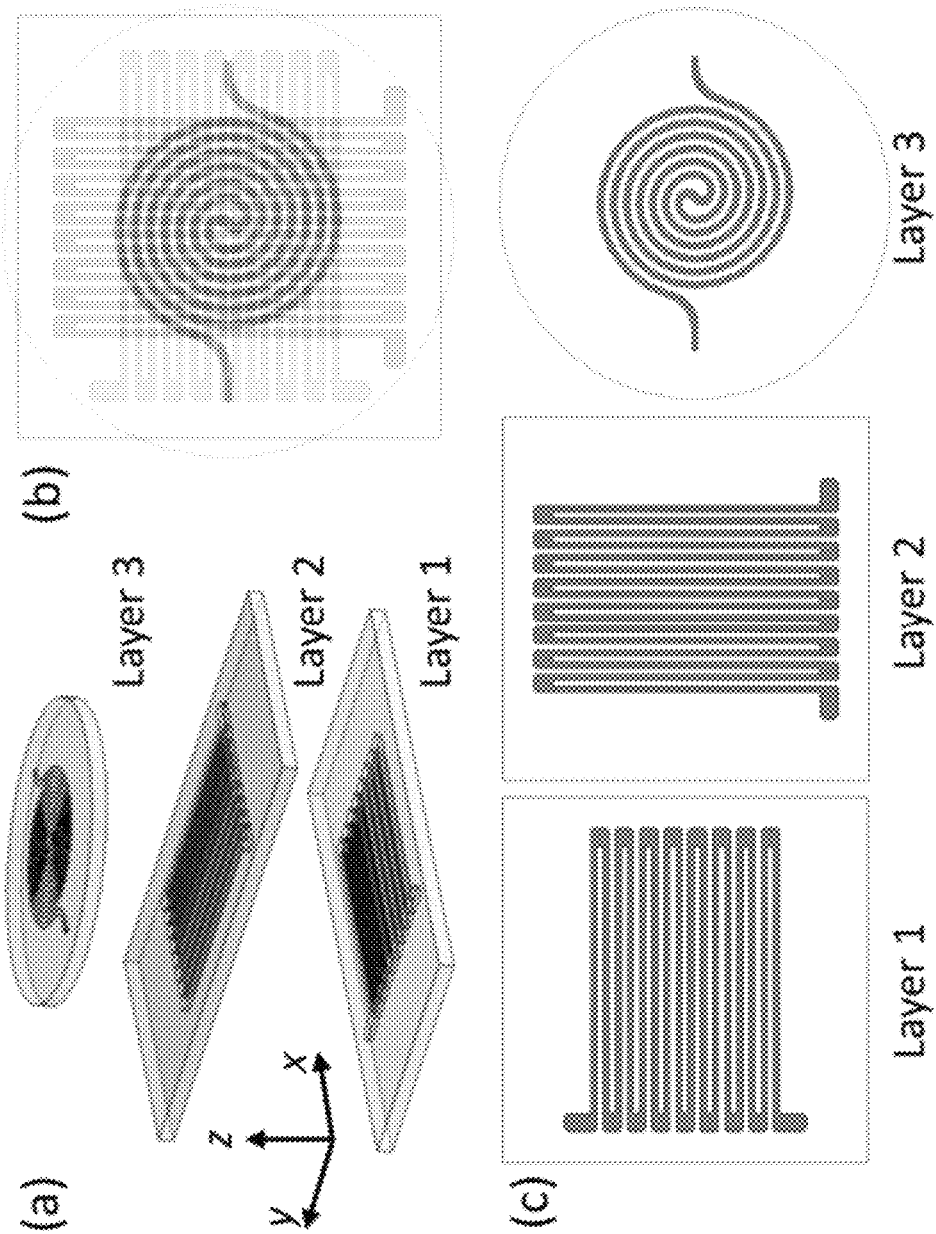
FIG. 6 shows a diagrammatic view of a multi-modal elastic strain sensor according to an embodiment of the invention.

FIG. 6 shows one embodiment of combination or multi-mode (strain and pressure/contact) sensor according to an embodiment of the invention. As shown in FIG. 6(a), the sensor according to this embodiment can be used to sense strain in the X and Y dimension and pressure in the Z dimension. FIG. 6(b) shows a top view of the multi-mode sensor according to an embodiment of the invention wherein the two unidirectional strain sensors are arranged with their strain axes orthogonal to provide strain sensing in the X and Y dimension and a pressure sensor is provided on the top layer to sense pressure in the Z dimension. FIG. 6(c) shows the individual layer patterns for the multi-modal sensor.

Figure 7:
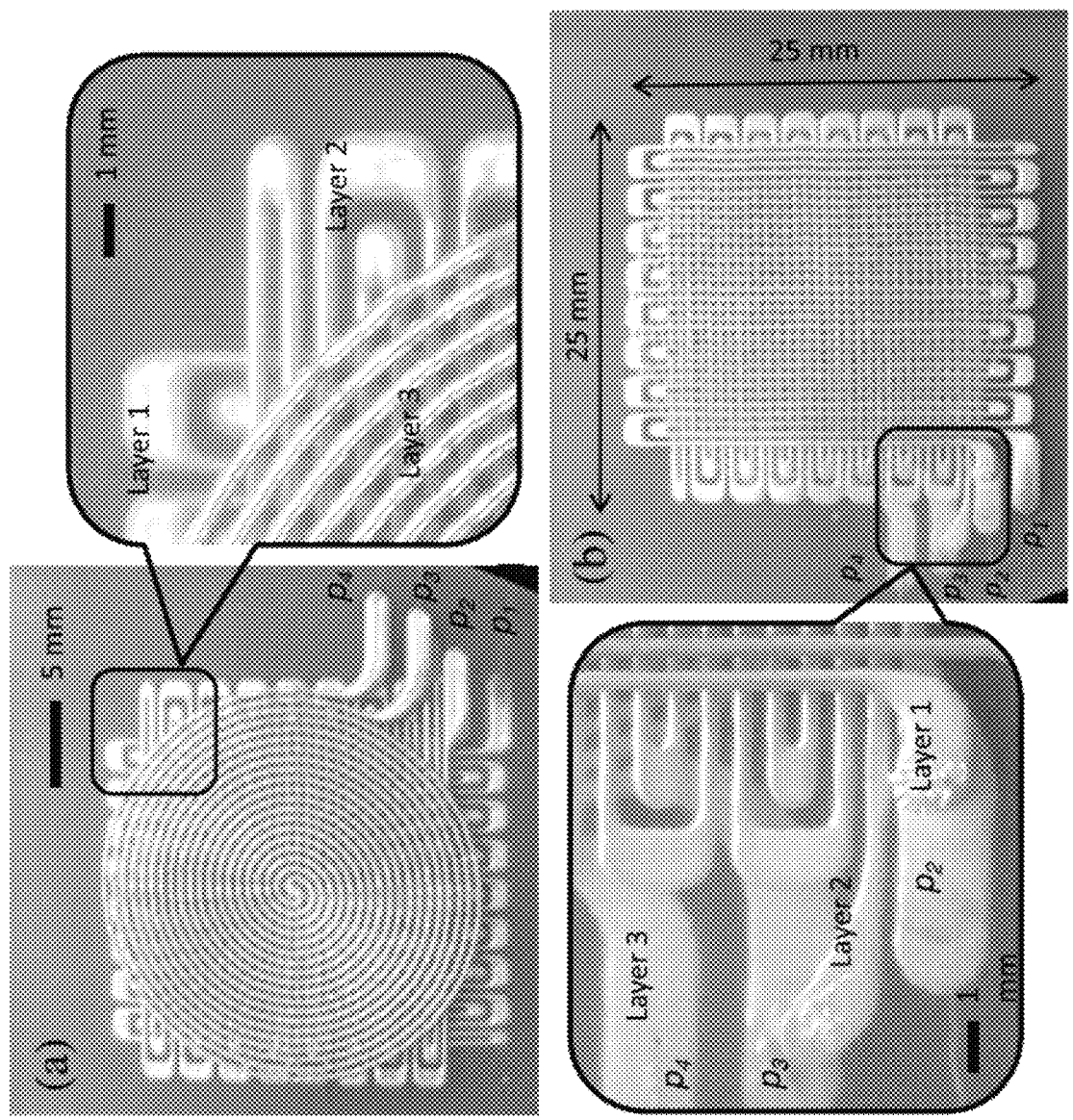
FIG. 7 shows a multi-modal elastic strain sensor according to an embodiment of the invention.

In accordance with one or more embodiments of the invention, a multi-modal sensor can include three soft sensor layers made of silicone rubber (FIG. 6) that is highly stretchable and soft (modulus: 69 kPa, shore hardness: 00-30). Layer 1 and 2 can include straight-line microchannel patterns that are sensitive to axial strains as well as to contact pressure and Layer 3 can include a circular pattern for pressure sensing but is not sensitive to axial strain. Layer 2 can be placed on top of Layer 1 with a 90-degree rotation for detecting strain along a perpendicular axis. Using the combination of the signals from the three sensors, the device can detect and distinguish three different stimuli: x-axis strain, y-axis strain, and z-axis pressure (see FIG. 6(a)). All three sensor layers can be connected through interconnects (p2 and p3 in FIG. 7) between layers, making one circuit that is electrically equivalent to three variable resistors connected in series.

Figure 8:
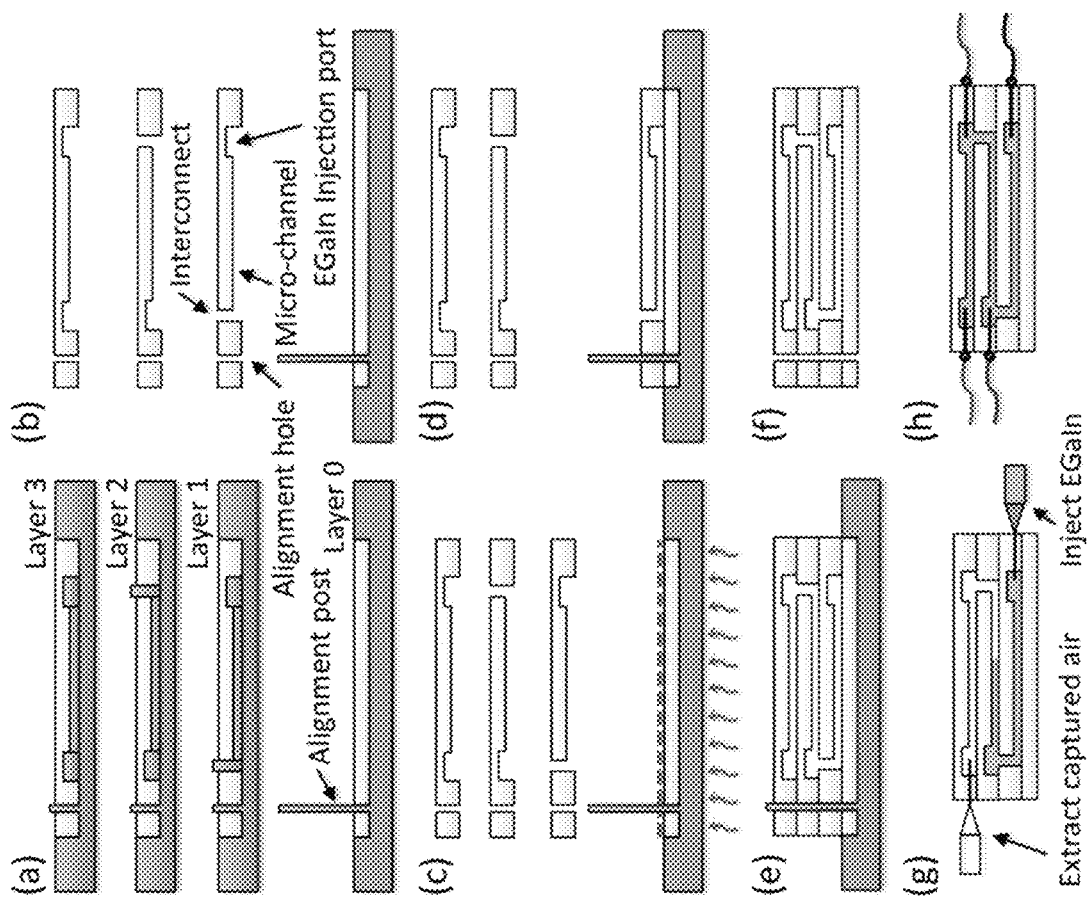
FIG. 8 shows a method of fabricating a multi-modal elastic strain sensor according to an embodiment of the invention.
Figure 9:
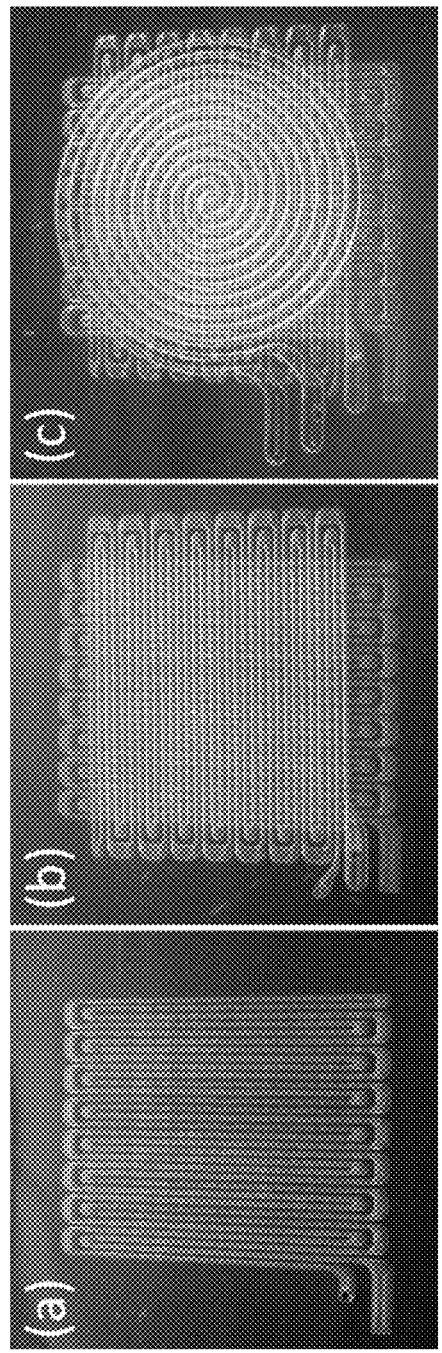
FIG. 9 shows layered views of a multi-modal elastic strain sensor according to an embodiment of the invention.

The multi-modal sensor can be fabricated using a layered molding and casting process, as shown in FIG. 8. The process can be divided into three steps, casting, bonding, and EGaIn injection. The base material can be an elastomer material, for example, silicone rubber (e.g., EcoFlex0030, Smooth-On, Inc., Easton, Pa.), which is chosen for its combination of high stretchability (elongation at failure: 900%) and ease of casting at room temperature. A relatively low mixed viscosity (3000 cps) is an additional consideration in order to successfully reproduce the features of the mold. The first step is to cast separate sensor layers (see FIGS. 8(a) and (b)). Plastic molds are prepared using a 3D printer (e.g., Connex500, Objet Geometries Ltd., Billerica, Mass.), and liquid silicone is poured into the molds. The second step is to bond layers to make a single sensor structure (see FIG. 8(c)-(f)). The cured layers are bonded by spin-coating liquid silicone between layers. Partial curing of the spin-coated silicone prevents the silicone from blocking microchannels. Also, alignment posts in the molds facilitate aligning the interconnects between layers. In the final step, EGaIn is injected into the microchannels and wire connections are made by inserting electrodes (see FIGS. 8(g) and (h)). FIG. 9 shows how each layer is bonded to the previous layer with alignment, as described in FIG. 8(c)-(e). In each bonding step, alignment is important to ensure the channel connection between layers through interconnects.

In accordance with one embodiment, a multi-modal sensor 100, as shown in FIG. 6, can be included as part of skin or outer covering for a moving component. In this embodiment, the channel dimensions can be 200 µm by 200 µm for strain sensing (Layer 1 and 2) and 200 µm (width) by 200 µm (height) for pressure sensing (Layer 3). The overall size of the artificial skin can be 25 mm by 25 mm, and the thickness can be approximately 3.5 mm.

Figure 10A:
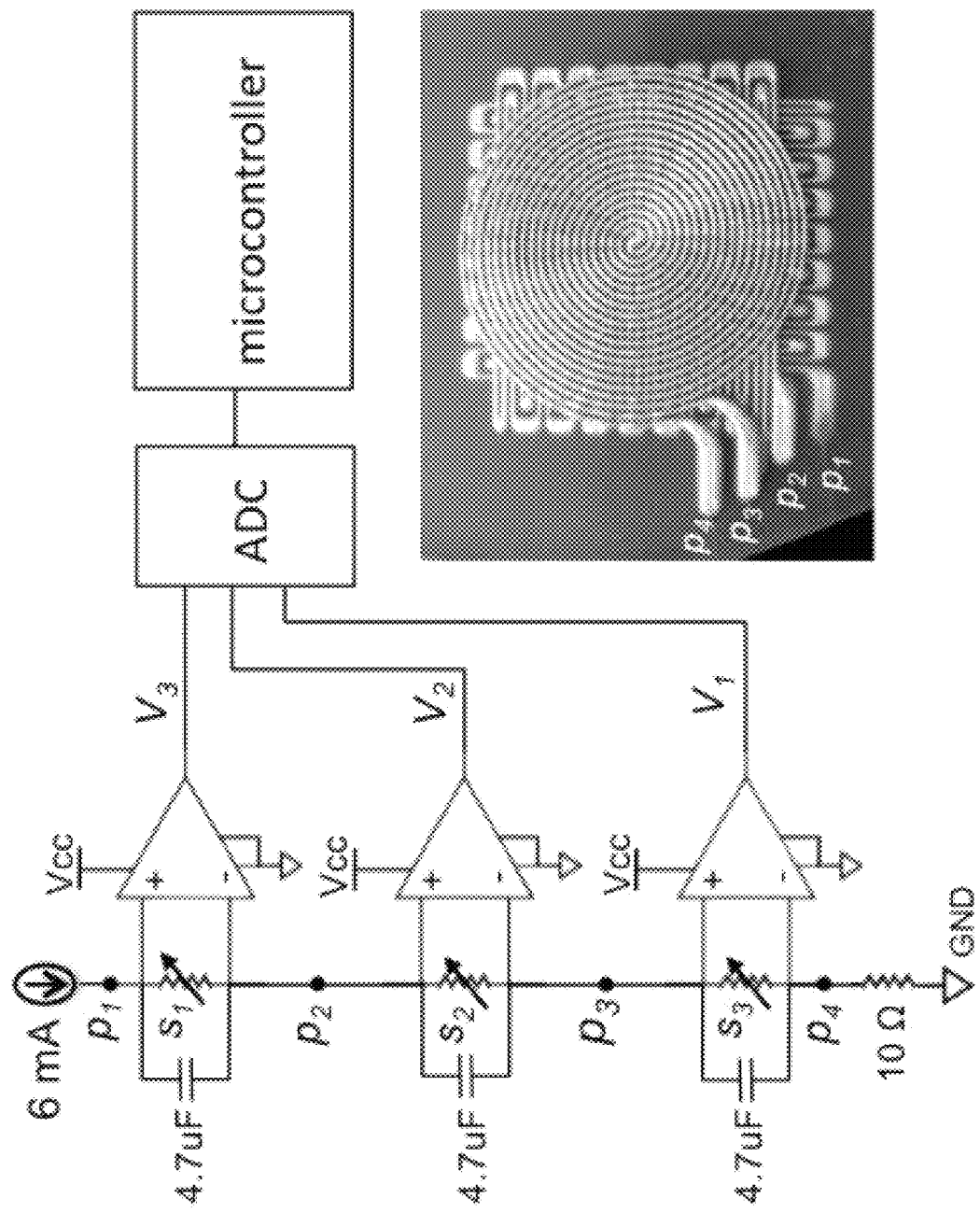
FIGS. 10A and 10B show a circuit diagram and test configuration for testing a multi-modal elastic strain sensor according to an embodiment of the invention.

FIG. 10A shows the circuit diagram that can be used to read signals from the three sensor layers. A constant current source can be used to generate constant current that flows through the three sensors in series, creating voltage drops at each sensor layer. The voltage difference across each sensor can be amplified by an instrumentation amplifier. The amplified signals can be connected to three analog-to-digital conversion ports of a microcontroller to separately measure the resistance changes.

Figure 10B:
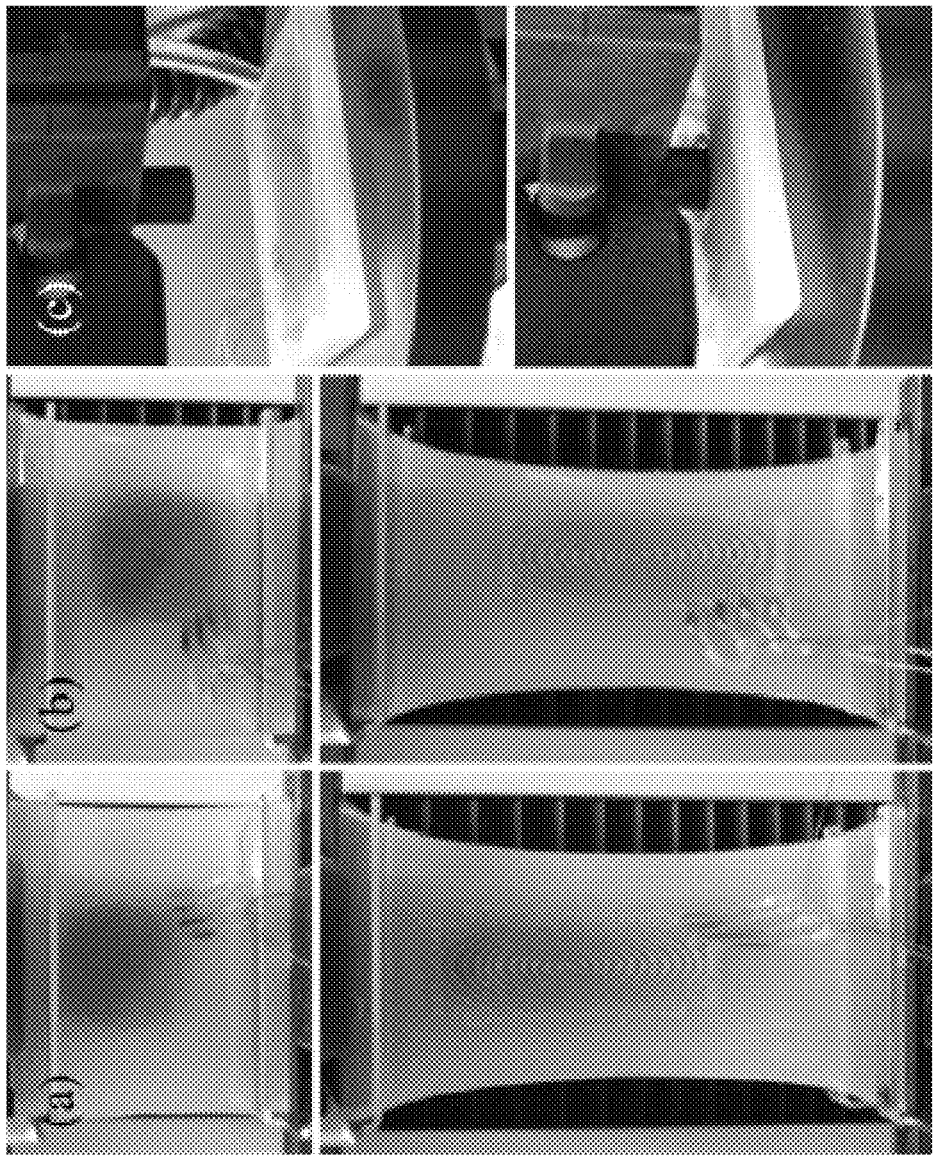
Figure 11A:
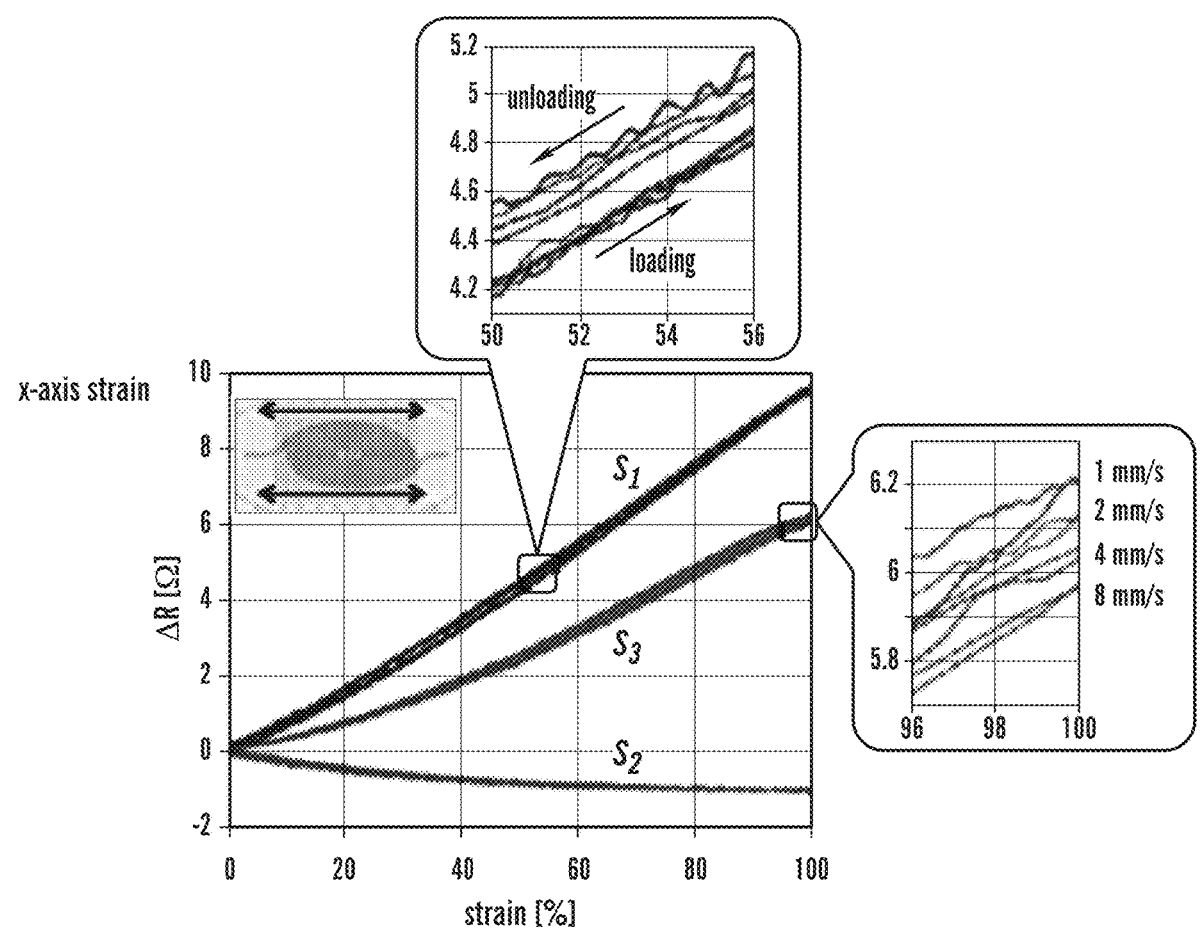
FIG. 11A, FIG. 11B, and FIG. 11C show graphs of the strain and sensor output of a multi-modal elastic strain sensor according to an embodiment of the invention.
Figure 11B:
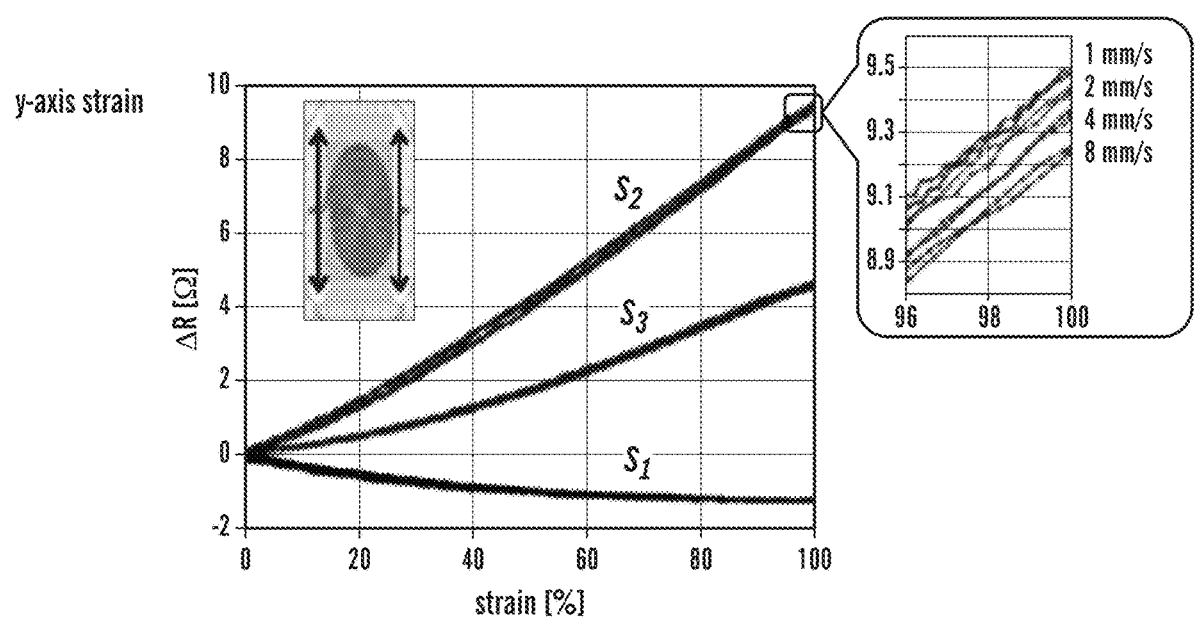
Figure 11C:
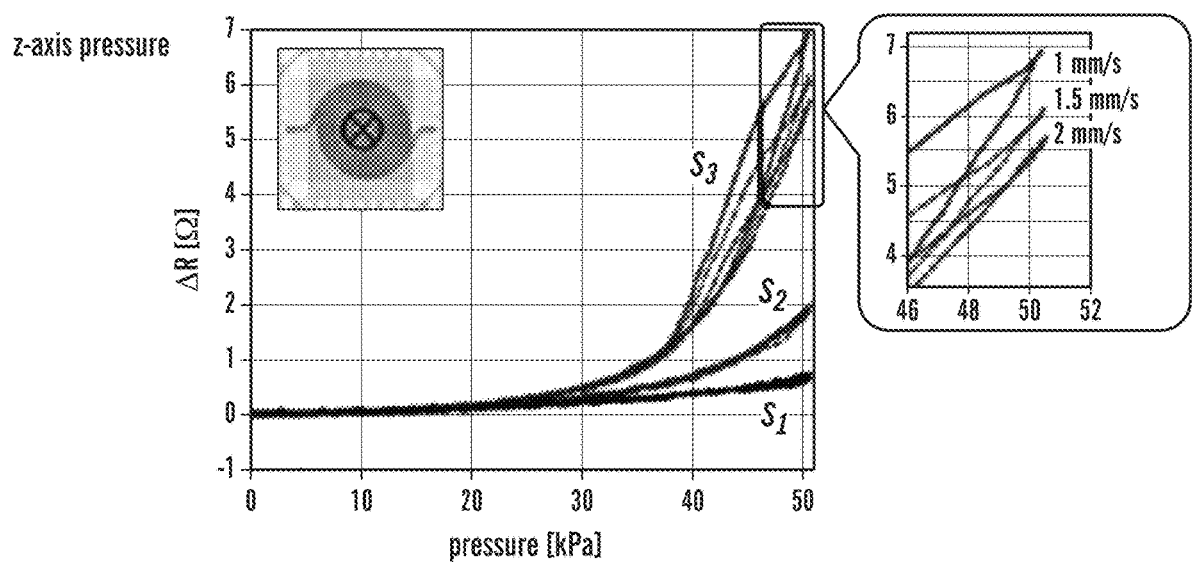

The multi-modal sensor can be calibrated by applying strains in multiple directions and contact pressure using, for example, a materials tester (e.g., Instron 5544A, Instron, Norwood, Mass.). In one embodiment of the invention, the multi-modal sensor can be stretched up to 100% in both x and y axes for strain sensing (FIG. 10B), and the center of the sensor can be compressed up to 60 kPa for pressure sensing. The results showed linearity in strain sensing and nonlinearity in pressure sensing as shown in FIGS. 11A-11C. FIG. 11A shows x-axis strain, FIG. 11B shows y-axis strain, and FIG. 11C shows y-axis pressure. However, the sensor signal was repeatable in both cases. Since the signals from the three sensor layers displayed different responses in each experiment, the prototype is able to not only measure the magnitudes of strains and pressure but also distinguish the types of stimuli.

In accordance with one embodiment of the invention, one or more of the multi-modal sensors can be incorporated in an artificial skin that provides sensory response without additional sensors. These artificial skins can be used for humanoid robots [31], robotic prosthetics [34], and soft wearable robots [32], [9].

Figure 12:
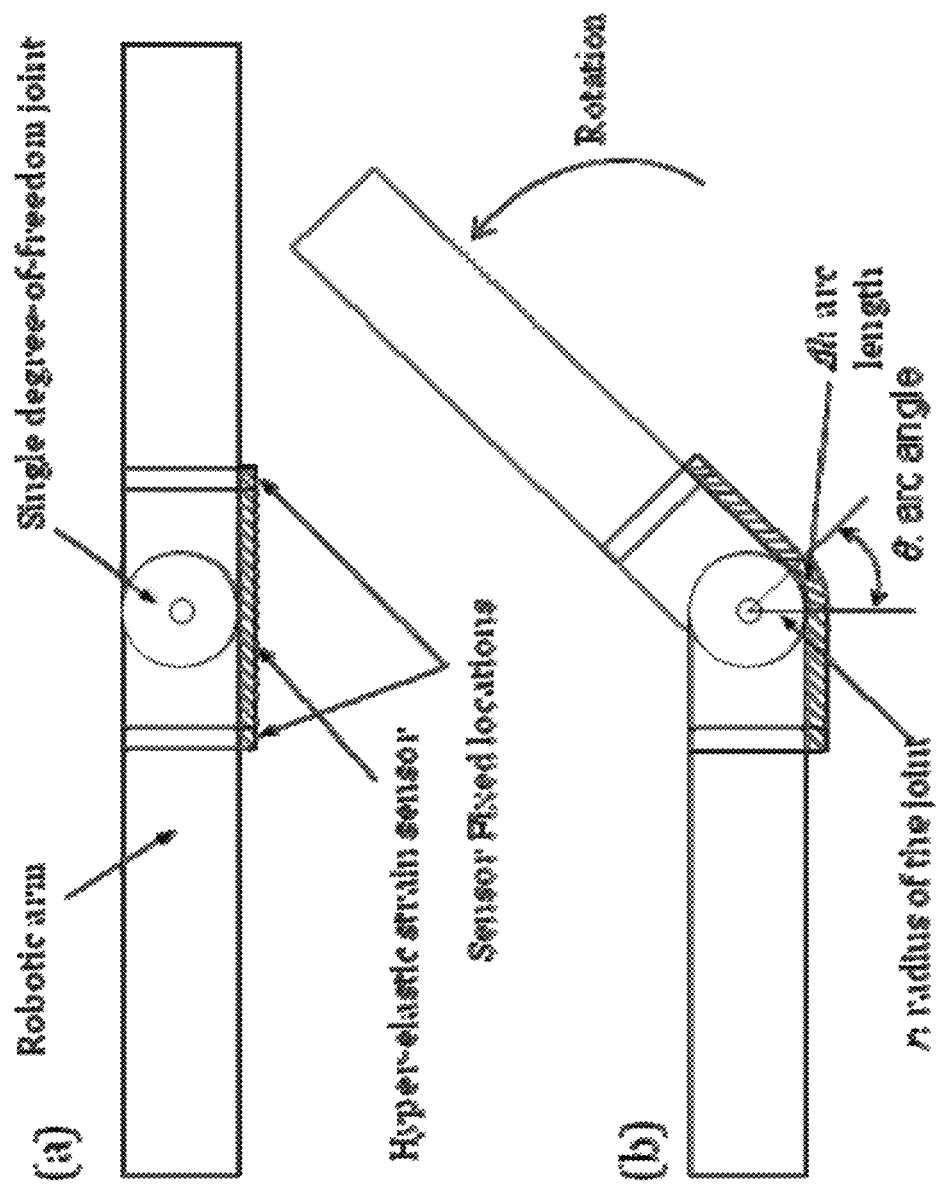
FIG. 12 shows an angle measurement of a single d.o.f. robotic arm using a hyper-elastic strain sensor according to an embodiment of the invention.

FIG. 12 shows an example of an elastic strain sensor according to an embodiment of the invention applied to measure the angular movements of a robotic arm. The strain sensor can be attached to the joint of a robotic arm that has at least one degree-of-freedom (d.o.f.). The two ends of the sensor can be fixed to the robotic arm, and the middle part can slide on the joint without friction. When the joint makes a rotation to bend the arm, the strain sensor can become stretched around the joint proportional to the arc angle. In this way, the arc angle can be easily measured by the elastic strain sensor according to an embodiment of the invention.

The arc length can be simply calculated as $\Delta l = r\theta$. Then, from equation 1, $\Delta R/R_0 = G\varepsilon$ and $\varepsilon = \Delta l/l_0$ where $\Delta R$ is the resistance change, $R_0$ is the original resistance, $G$ is the gauge factor, and $\varepsilon$ is the strain. Assuming there is no temperature change, the angular change ($\theta$) can be determined as following:

$$\theta = \frac{l_0 \Delta R}{G R_0 r} \tag{6}$$

where $l_0$ is the original length of the strain sensor. The strain response of the sensor can be determined empirically, from the calibration experiment and shown to be linear (FIG. 3), which means $G$ is a constant, and $l_0$, $R_0$, and $r$ are all constants, the angular position of the robotic arm can be linearly proportional to the resistance change of the sensor.

Figure 13:
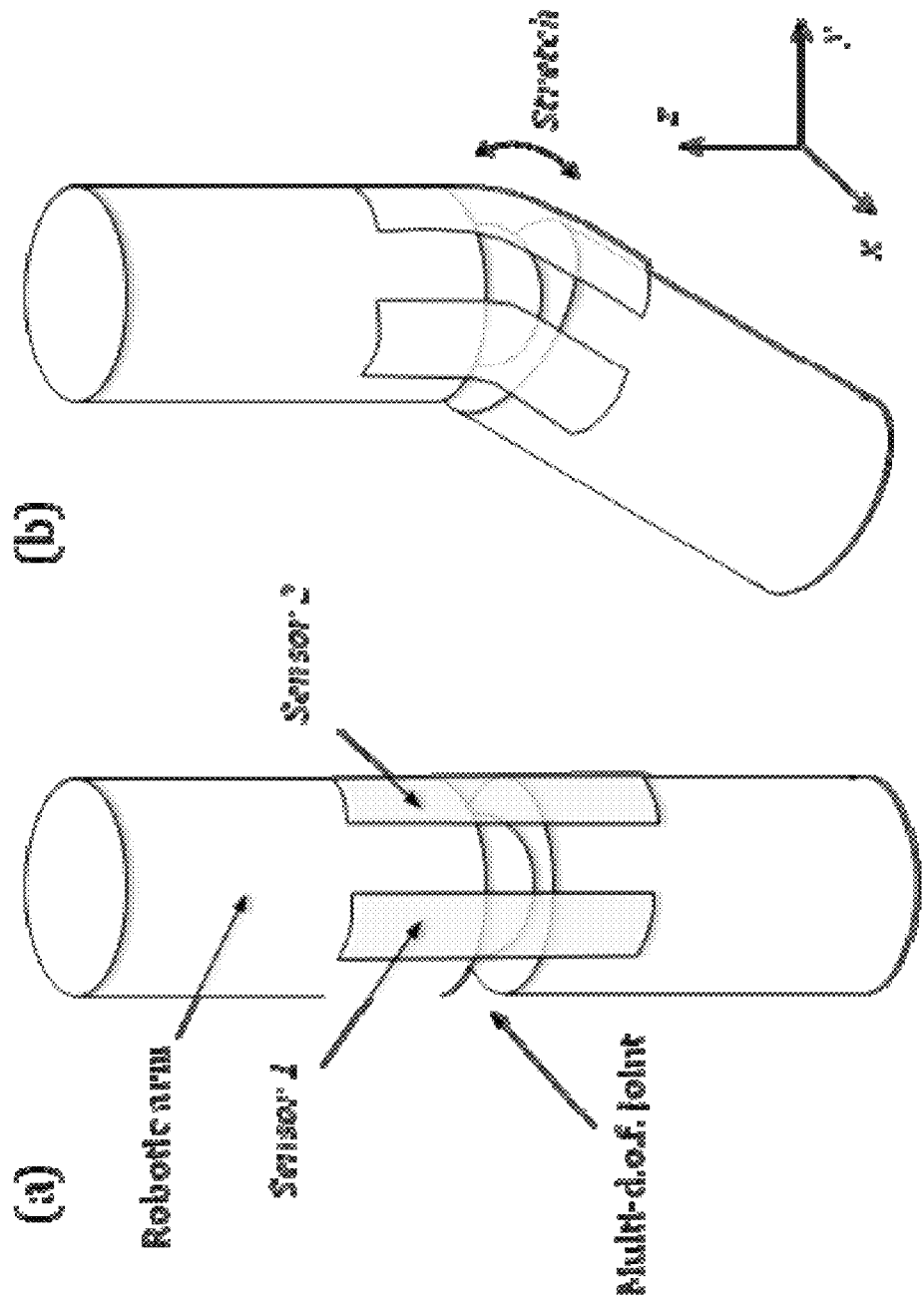
FIG. 13 shows an angle measurement of a multi-d.o.f. robotic arm using a hyper-elastic strain sensor according to an embodiment of the invention.

In accordance with an embodiment of the invention, motion sensing can be expanded to measure the angular position of the robotic arm in 3D motions (multiple d.o.f.s) by adding more sensors to different locations, as shown in FIG. 13. Assuming the robotic joint in FIG. 13 has only two d.o.f.s., the minimum number of sensors needed for measuring 3D angular positions is two, although more sensor can be used. Where the sensor signal for strain change is linear, we can construct a simple matrix to calculate the joint angles such as $$\begin{bmatrix} \theta_{xz} \\ \theta_{yz} \end{bmatrix} = C \cdot \begin{bmatrix} s_1 \\ s_2 \end{bmatrix} \tag{7}$$

where are $\theta_{xy}$ and $\theta_{yz}$ are angles of the robotic arm projected to xz and yz planes, respectively, and $s_1$ and $s_2$ are sensor signals from sensors 1 and 2, respectively. C is a calibration matrix (2×2 in this example), and it can be found experimentally.

Figure 14:
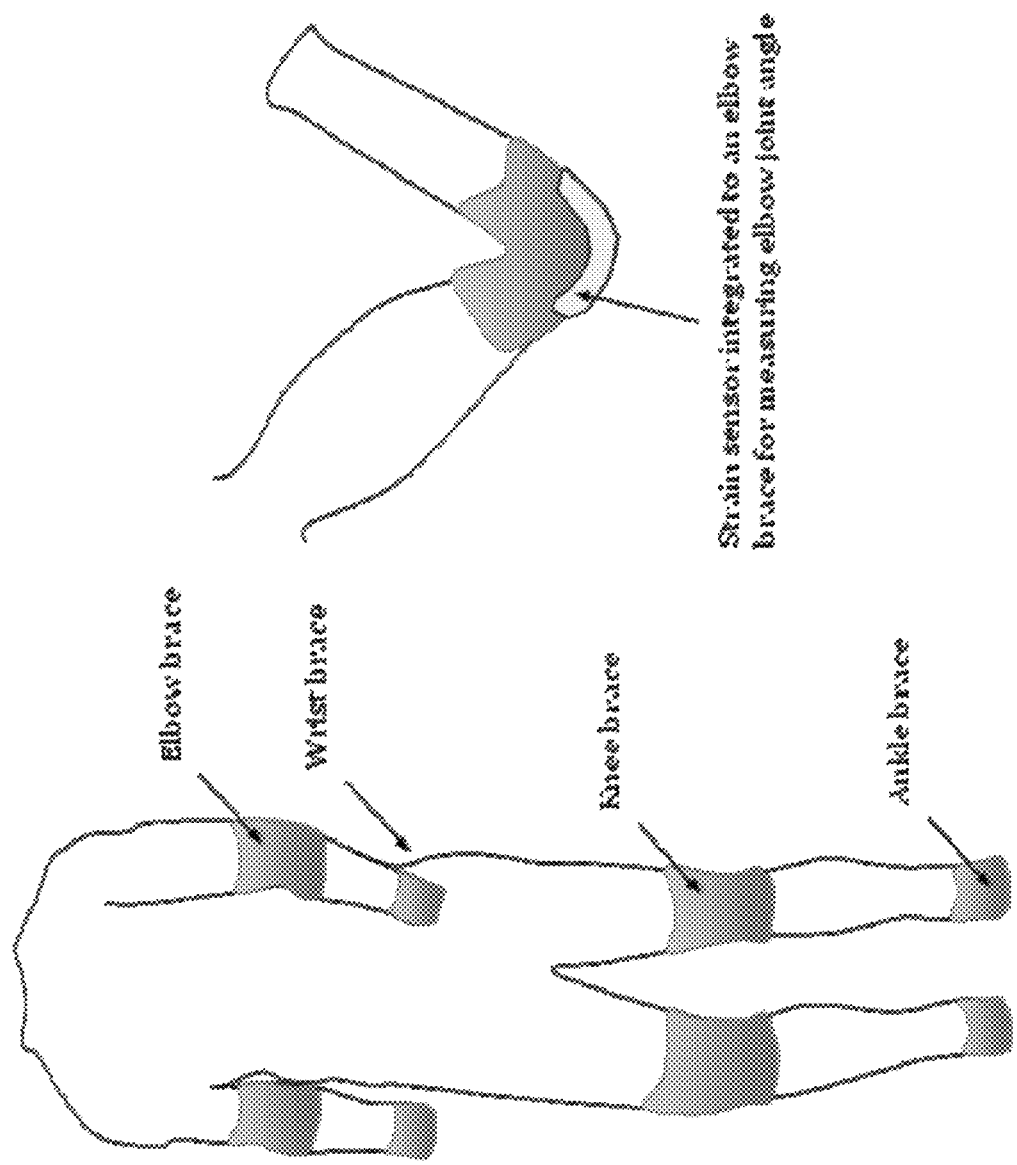
FIG. 14 shows a stretchable body suit for measuring body joint angles using one or more hyper-elastic strain sensor according to an embodiment of the invention.
Figure 15:
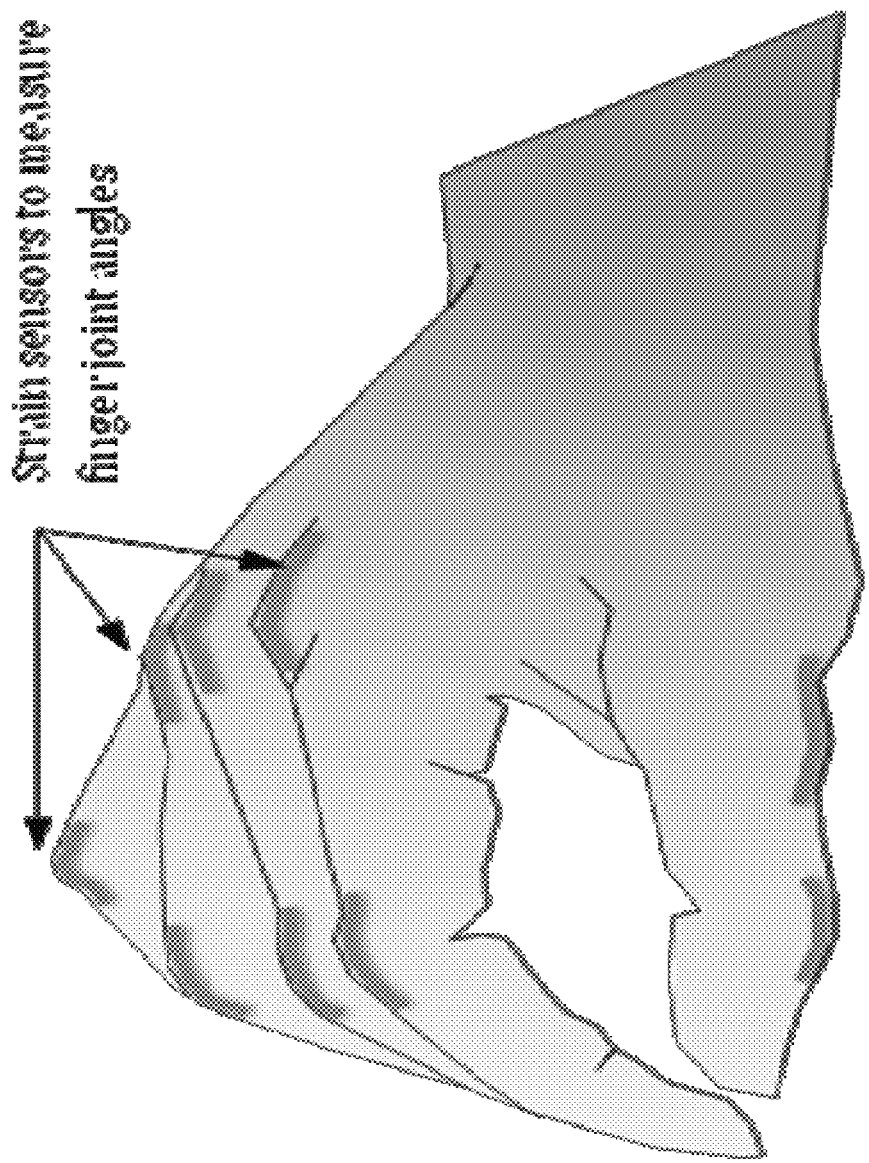
FIG. 15 shows a stretchable glove with strain sensors for measuring finger joint angles using one or more hyper-elastic strain sensor according to an embodiment of the invention.

In accordance with embodiments of the invention, the application of the strain sensor is not limited to a robotic joint. The sensors according to the invention can be used to measure the joint angles of human bodies. The highly soft and stretchable properties of the sensors according to the invention make the sensor easily conformable to complicated shapes of different human bodies. FIG. 14 and FIG. 15 show examples of applying the strain sensor to acquire joint angle information. In these embodiments, the multi-modal sensors according to the various embodiments of the invention can be used to measure more complex joint motion than shown in FIG. 12 and FIG. 13.

The present invention can be used in a system for evaluating biomechanics using the flexible strain and pressure sensors described herein.

In accordance with one embodiment of the invention, the system uses the flexible sensors to detect and measure strain, pressure, shear, and curvature of a biomechanical system such as a joint or set of joints of a subject under study. As described herein, the flexible sensors incorporate microchannels, filled with a conductive liquid metal alloy as shown in FIGS. 1, 2, 4, 6 and 7. For the strain sensor, when the flexible material experiences strain in the axial direction of the micro-channels, the overall channel length increases and the cross-sectional areas of the channels decrease, causing an increase in the overall measured resistance. The measured resistance can be calibrated with a joint angle for this sensor in order to provide a direct measurement of the angle of the given joint with respect to one of the limb segments. In addition, one or more pressure sensors can be provided in an insole of a shoe worn by the subject in order to measure the applied external forces to the environment.

In accordance with one embodiment of the invention, a modular sensor system can be provided whereby each joint (e.g., ankle, knee, hip, wrist, elbow, shoulder, etc.) or rigid body (e.g., hand, forearm, foot, shank, thigh) can be fitted with a separate sensor subsystem or module. Each sensor subsystem can include a flexible brace with one or more flexible sensors, one or more processors, and one or more energy sources (battery, or motion-generated power). The user could choose to use one or more of the sensor modules on one or more joints or rigid elements of the subject depending on the desired application.

In accordance with one embodiment of the invention, a hybrid brace system can be provided whereby each joint or rigid body can be fitted with a subsystem or module. Each subsystem can include one or more flexible braces, one or more flexible sensors, one or more processors, and one or more batteries, as well as one or more force sensors, bend sensors, pressure sensors, torque sensors, tilt sensors, accelerometers, gyroscopes, magnetometers, and/or optical sensors. This hybrid system with additional sensing modalities can be appropriate for certain applications.

In accordance with one embodiment of the invention, a hybrid shoe system can be provided. The hybrid shoe system can include one or more flexible sensors to obtain ankle angles and includes one or more additional sensors, such as force sensors, pressure sensors, torque sensors, tilt sensors, accelerometers, gyroscopes, magnetometers, and/or optical sensors, in order to infer stride length and running speed, in addition to the associated ankle biomechanics.

In accordance with some embodiments of the invention, the pure strain and/or hybrid (e.g., strain and pressure) embodiments can include a soft, flexible garment that serves to properly position the sensors relative to the desired anatomical structures of the subject. These garments can include rigid support elements or structures to assist in garment stabilization. In addition, depending on the application, the support elements or structure may or may not affect the range of motion of the subject. In some embodiments of the invention, the garment can be separable from the sensors and electronics for easy wash ability.

In accordance with some embodiments of the invention, the system can be untethered, for example, the controller and the batteries can be a part of the system worn by the subject without the need for wires to connect to a separate off-body laptop/desktop/plug-in power supply, etc. Wireless communications, such as WiFi, Blue Tooth, Zig Bee, can be used to transfer data between the controller worn on the subject and a remotely located computer. In some embodiments of the invention, each sensor can have an individual power, processer and transceiver components, and in other embodiments the sensors can be tethered (e.g., wired or wirelessly connected) to a single electronic device that is meant to be worn by the subject and which will provide power, processing and wireless data transmission for all sensors.

In accordance with some embodiments of the invention, the control signals sent to the sensor system and motion data measured by the sensor system can be wirelessly transmitted under software control on a computer and transmitted to a secure data storage site.

In other embodiments, one or more sensor outputs can be input into a computer/processor running a biomechanical model (e.g., a software program) and this model can be used to generate estimates of limb segment motion and orientation.

In accordance with the invention, the calibration for each of these embodiments can be activity and limb-segment dependent. Thus, a calibration routine may be needed for some or all activities that use the sensor system. In addition, for applications, a higher-fidelity calibration can be used, for example, for rehabilitation applications as compared to game/computer interface applications.

Figures 20A, 20B, 20C:
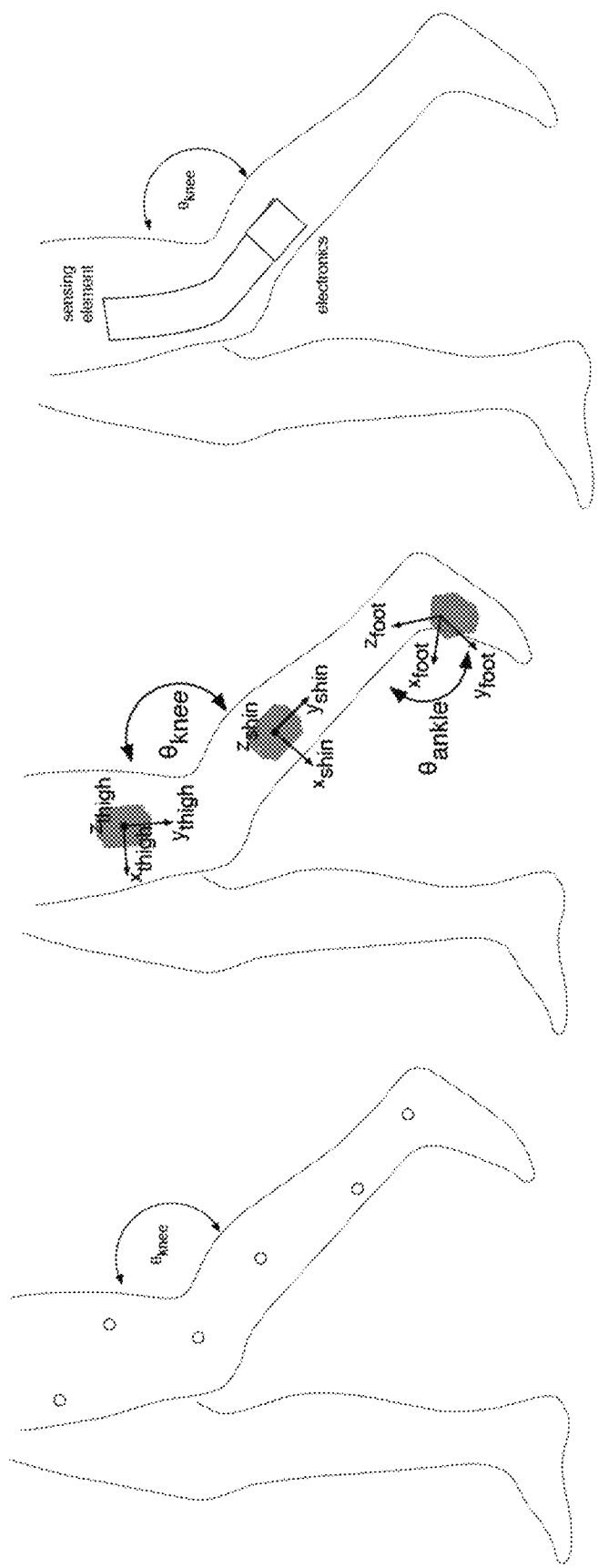
FIGS. 20A and 20B show instrumentation and placement of sensors in prior art systems for determining joint angle.
FIG. 20C shows a flexible system for measuring joint angle according to one embodiment of the invention.

FIGS. 20A and 20B show various prior art systems for evaluating biomechanics. FIG. 20A shows a system that uses passive or active visual markers that are used in making a video recording of a subject performing a task. The visual markers are positioned to enable a clinician, as well as software applications, to evaluate the video recording to study the biomechanics of the subject. FIG. 20B shows a system that uses inertial measurement devices, positioned on the subject for the same. The motion data determined by the inertial measurement devices can be processed to evaluate motion. FIG. 20C shows a system according to the invention, wherein a flexible sensor is positioned on the joint to measure the angle of the joint based one strain experienced by the sensor as the joint is flexed and extended.

FIG. 21 shows an example of a system according to the invention for monitoring the forces and motion of a joint. In this example, the system can measure the forces experienced by the foot. In this embodiment, the sensors, force sensor 2 and kinematic sensor 3 can be mounted to a neoprene sock 1 that is worn by the subject. The neoprene sock 1 can include a zipper 4 for easy removal as well as one or more rigid or semi-rigid support elements (not shown). The sensors 2 and 3 can be connected by wires to the controller 5 that includes a power source such as a battery. The controller 5 can communicate wirelessly to computerized device 6 such as a desktop or portable computer, a smart phone or tablet computer, executing one or more software programs to receive the sensor data and provide, for example an assessment of the motion detected.

Figure 22B:
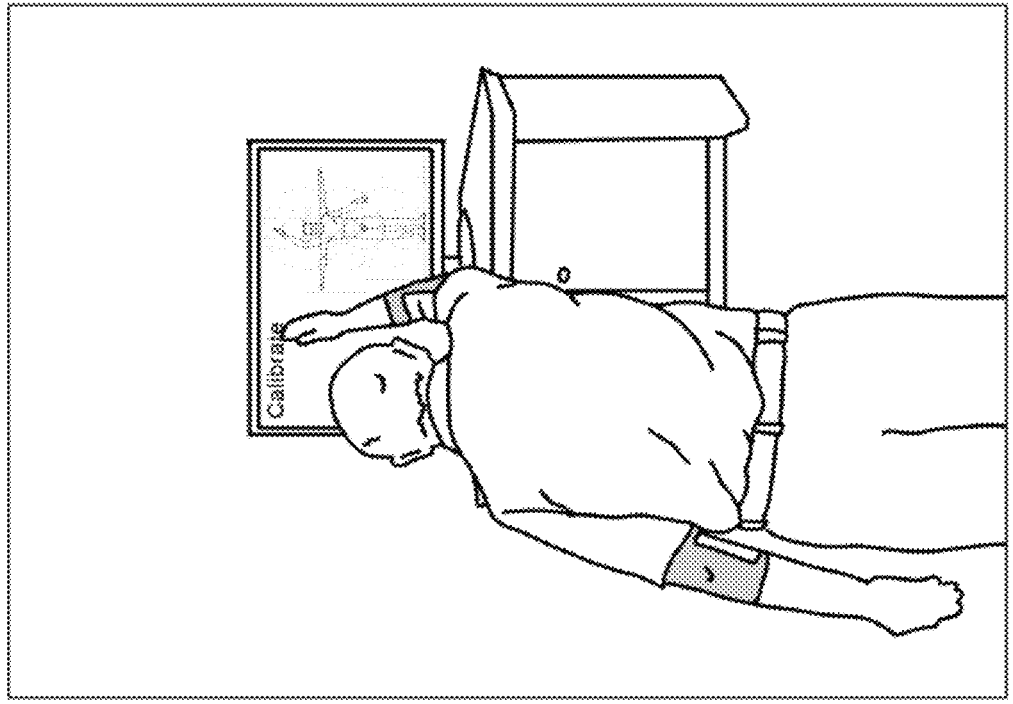
FIGS. 22A-22E show a sensory system according to one of the embodiments of the invention used in various applications.
Figure 22A:
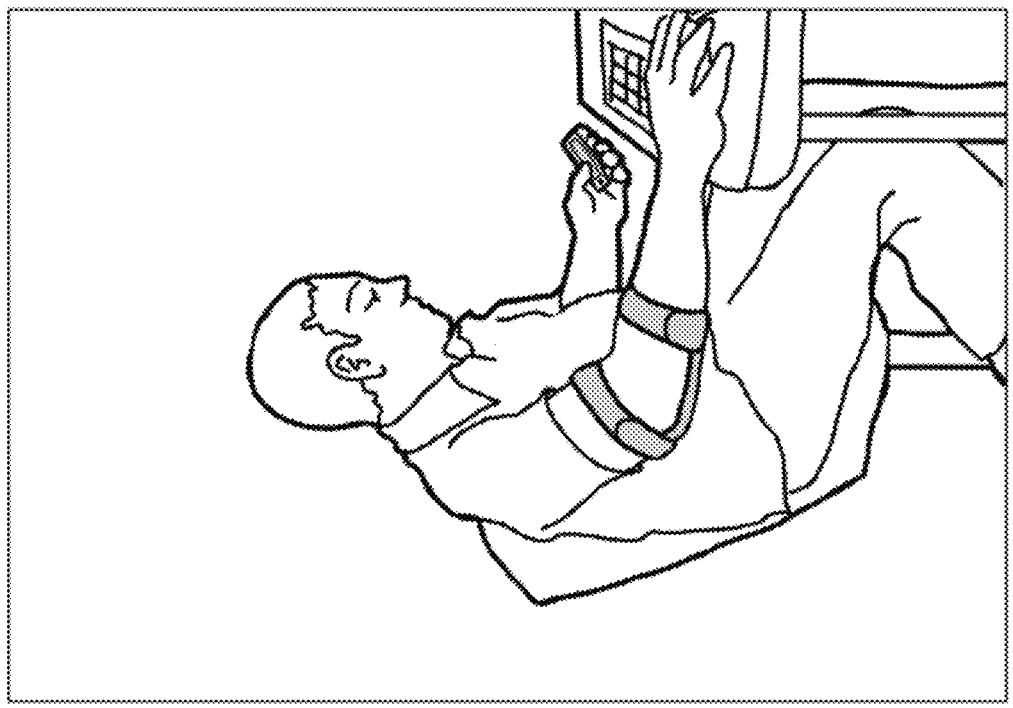
Figure 22E:
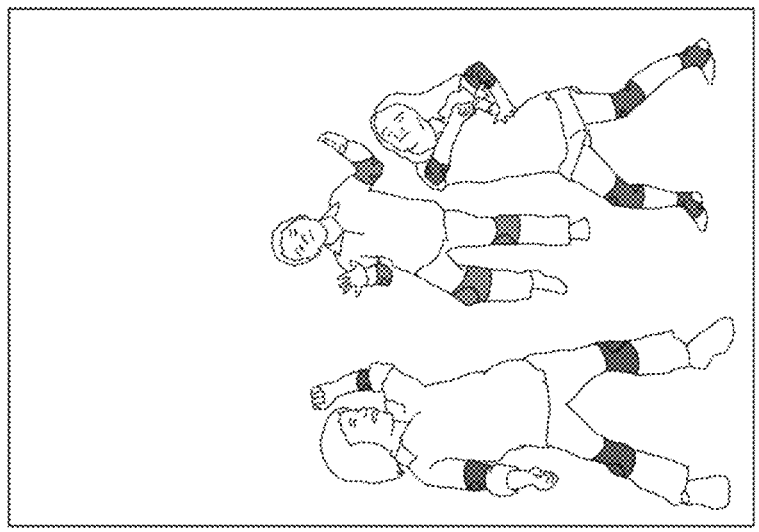
Figure 22D:
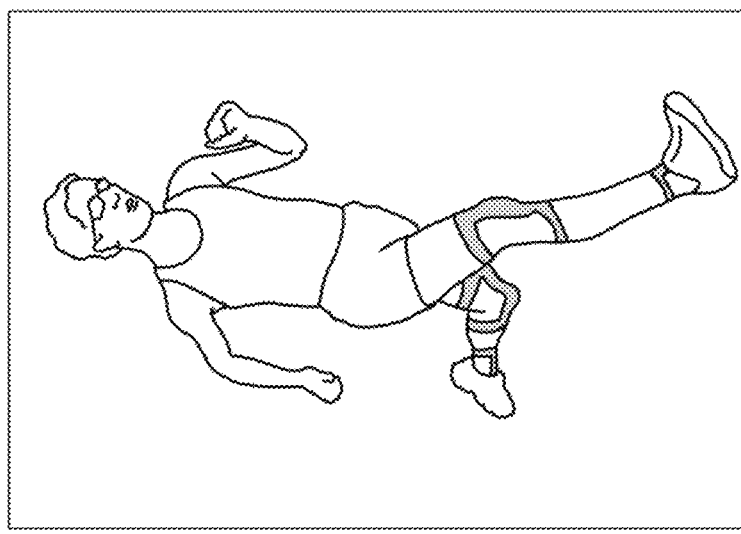
Figure 22C:
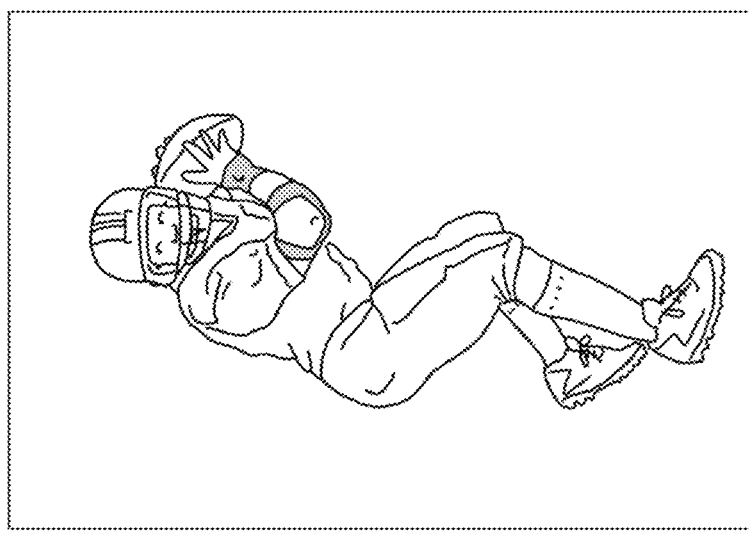

FIGS. 22A-22E shows various examples of application for the use of the sensor system according to the invention. FIGS. 22A and 22B show rehabilitation applications. FIGS. 22C and 22D show rehabilitation applications in the context of assessing performance. FIG. 22E is one example of a computer game interface application.

FIG. 22A shows an elbow rehabilitation system worn by a subject. The system can transmit data to the subject's mobile phone, which can forward the exercise data to a care provider. The system can notify the subject via a smartphone app as to when to perform rehab tasks as well as guide the subject through the prescribed routine. FIG. 22B shows an elbow rehabilitation device with an interface for performing required motions. In this embodiment, the sensor system can communicate with a computer system (e.g., a desktop/ laptop, or system embedded in a TV, smart phone or other computerized device) to enforce and monitor physical and/ or occupational therapy. In these embodiments, the sensor system can be embodied in a brace work over a subject's joint, such as an elbow or wrist. The sensor system can include one or more flexible sensors mounted in brace positioned on the joint to measure changes in joint angle.

The joint angle data can be stored on the controller and communicated to a remote device.

FIG. 22C shows a multi joint (e.g., shoulder, elbow, and wrist) monitoring system comprised of a set of braces worn on each joint (or a single brace, like a sleeve extending from the wrist to the shoulder) that can measure the performance of each individual joint during a sporting activity. The performance data can be stored locally on the device for retrieval after the sporting activity is completed, or it can be wirelessly transmitted to a remote computer at various times during the activity. Thus, after a football game or tennis match, the subject and/or a care giver can analyze the movement data and assess the performance of the subject.

FIG. 22D shows a multi joint (e.g., knee and ankle) monitoring system comprised of a set of braces worn on each joint (or a single brace, like a sleeve extending from the ankle to the hip) that can measure the performance of each individual joint during a sporting activity. The performance data can be stored locally on the device for retrieval after the sporting activity is completed, or it can be wirelessly transmitted to a remote computer at various times during the activity. Thus, after a run or a soccer game, the subject and/or a care giver can analyze the movement data and assess the performance of the subject.

FIG. 22E shows a sensor system for use as a computer game interface. In this embodiment, sensor braces or bands can be worn by the users on their joints, such that motion of any monitored joint can be detected. The motion of a specific joint can be interpreted by a computer game console to control some portion of the game. For example, monitoring braces worn on wrists, elbows, knees and ankles can be used to report joint angles to a computer gaming system. The joint angle input can be used to evaluate the user motion, for example, dancing or running in the context of the game.

The sensor platforms previously described can be implemented for many applications, including rehabilitation, clinical motor assessment, drug delivery assessment, biomechanics and motion analysis, computer and game interface, human modeling and self-evaluation for performance improvement.

In accordance with some embodiments of the invention, the sensor systems can be used in rehabilitation applications, including tele-rehabilitation applications. In accordance with the invention, patients can wear the modular unit(s) on the joint(s) that they are working to rehabilitate to track their recovery progress. For example, after ACL surgery, a modular unit designed for the knee would be worn during physical therapy and during rehabilitation exercises at home. The physical therapist can compare the amount of time exercised and the resulting performance. In cases where insurance does not cover multiple physical therapy sessions, a therapist can check the progress of the patient as they perform at home by logging into a secure data storage site to which the data has been uploaded. Further, the braces can be bundled with customized computer or smartphone applications for patient recovery. The apps provide real-time visualizations to follow a self-guided rehabilitation program and also provide real time alerts if a patient is favoring a non-injured joint.

In accordance with some embodiments of the invention, the sensor systems can be used in clinical motor assessment applications, for example clinical research. Research is ongoing in the field of electrical and mechanical assistance for improving pathologies associated with motor control. The systems according the invention can be used to provide information regarding the patient's motor control with and without the assistive device. This additional information can be used for clinical assessment and evaluation of the efficacy of new assistive devices.

In accordance with some embodiments of the invention, the sensor systems can be used in drug delivery assessment applications. Implantable neurological stimulators and implantable drug pumps show promise in the treatment of a variety of diseases and ailments. Setting therapeutic levels and dosages is still difficult because it often relies on a clinician's observation of symptoms, or a patient's self-report of symptoms, such as tremors, during a dosage paradigm that can take hours, weeks, or months. The sensor system embodiments according to the invention can provide continuous monitoring of motor parameters and provide information to assess the tuning of the drug delivery for individuals.

In accordance with some embodiments of the invention, the sensor systems can be used in biomechanics applications, including in the field (outside the lab or clinic) applications. Current methods for motion analysis limit the ability to collect data outside of the lab environment. Systems according to the invention can be used to obtain biomechanical measurements during real situations as opposed to simplified or simulated laboratory exercises. For example, the modular system according to the invention can be used to further evaluate therapy and treatment strategy in sports medicine as the flexible garments encasing the sensors are similar to braces commonly worn during games. In addition to strategy, a more thorough understanding of sports injury can be developed. Currently injuries can be assessed by performing biomechanics analyses before or after the injury. Using the embodiments described here, athletes could wear the sensing system while playing. Then if an injury occurs, the evaluation could be made based on the biomechanics at the time of injury. This would be beneficial for many common injuries that are not well understood, such as runner's knees, Achilles tendon injuries, ACL sprains and tears, etc. In addition to sports activities, injuries in other activities, such as music, dance or occupational maladies could be further understood. For example, injuries such as carpal tunnel syndrome in piano players, muscle contractures during violin playing, and knee injuries in dancers could be studied to improve technique and reduce injury as well as to optimize rehabilitation after injury.

In accordance with some embodiments of the invention, the sensor systems can be used in computer and game interface applications. Many gaming systems are moving towards motion based system control. By using the modular sensor system, an interface to a gaming system or computer can be developed to control software programs based on the directly measured motions of the user. In this embodiment, the number of sensors can be minimized by selecting the least number of sensors needed for the game application. Further, in a related application, a specialized computer interface could be developed that permit a disabled user to control a computer system using limited biomechanical functionality.

In accordance with some embodiments of the invention, the sensor systems can be used in Human Modeling. The sensor system according to the invention can be used to obtain information about the body in combination with other sensors or sensor systems. For example, coupling inertial data with joint angle information can lead to a better prediction of the mass and inertia properties of the body. In another example, by applying a known force to the biomechanical system with the strain sensors, one can obtain an estimate of the joint stiffness. Inversely, by applying an additional known stiffness to the joint, one can obtain information on the dynamic force production ability of the user.

In accordance with some embodiments of the invention, the sensor systems can be used in personal performance system applications. There are an increasing number of personal systems for self-evaluation, including pedometers and accelerometers for evaluating a person's steps per day or running speed. The sensor system according to the invention can be part of a platform can provide individuals with personal performance information for self-training and evaluation using real-time feedback. For example, marathon trainers could see how their biomechanics change due to fatigue. Similarly, skill-acquisition that requires a focus on body posture and positioning (e.g., dance, kung-fu, tai chi, yoga, golf, basketball, football, soccer, etc.) could be improved.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

The following references are cited in the text. Each of the following references is hereby incorporated by reference in its entirety.
1. Marculescu D et al 2003 Electronic textiles: a platform for pervasive computing *Proc. IEEE* 91 1995-2018
2. Stirling L, Yu C-H, Miller J, Wood R, Goldfield E and Nagpal R 2010 Applicability of shape memory alloy wire for an active, soft orthotic *Proc. Int. Conf. Shape Memory and Superelastic Technologies (Pacific Grove, Calif.)* pp 20-1
3. Rogers J A and Huang Y 2009 A curvy, stretchy future for electronics *Proc. Natl Acad. Sci. USA* 106 10875-6
4. Khang D-Y, Jiang H, Huang Y and Rogers J A 2006 A stretchable form of single-crystal silicon for high-performance electronics on rubber substrates *Science* 311 208-12
5. Kim D-H, Ahn J-H, Choi W M, Kim H-S, Kim T-H, Song J, Huang Y Y, Liu Z, Lu C and Rogers J A 2008 Stretchable and foldable silicon integrated circuits Science 320 507-11
6. Dickey M D, Chiechi R C, Larsen R J, Weiss E A, Weitz D A and Whitesides G M 2008 Eutectic gallium-indium (EGaIn): a liquid metal alloy for the formation of stable structures in microchannels at room temperature Adv. Funct. Mater. 18 1097-104
7. So J-H, Thelen J, Qusba A, Hayes G J, Lazzi G and Dickey M D 2008 Reversibly deformable and mechanically tunable fluidic antennas Adv. Funct. Mater. 18 1097-104
8. Kim H-J, Son C and Ziaie B 2008 A multiaxial stretchable interconnect using liquid-alloy-filled elastomeric microchannels Appl. Phys. Lett. 92 011904
9. Duffy D C, McDonald J C, Schueller O J A and Whitesides G M 1998 Rapid prototyping of microfluidic systems in poly(dimethylsiloxane) Anal. Chem. 70 4974-84
10. Unger M A, Chou H-P, Thorsen T, Scherer A and Quake S R 2000 Monolithic microfabricated valves and pumps by multilayer soft lithography Science 288 113-6
11. Quake S R and Scherer A 2000 From micro- to nanofabrication with soft materials Science 290 1536-40
12. Hoshi T and Shinoda H 2006 Robot skin based on touch-area-sensitive tactile element Proc. IEEE Int. Conf. on Robotics and Automation (ICRA '06) (Orlando, Fla., May 2006) pp 3463-8
13. Chigusa H, Makino Y and Shinoda H 2007 Large area sensor skin based on two-dimensional signal transmission technology Proc. IEEE EuroHaptics Conf. and Symposium on Haptic Interfaces for Virtual Environment and Teleoperator Systems (WHC '07) (Tsukuba, Japan, March 2007) pp 151-6
14. Yoshikai T, Fukushima H, Hayashi M and Inaba M 2009 Development of soft stretchable knit sensor for humanoids' whole-body tactile sensibility Proc. IEEE-RAS Int. Conf. on Humanoid Robots (ICHR '09) (Paris, France, December 2009) pp 624-31
15. Cotton D, Graz I M and Lacour S P 2009 A multifunctional capacitive sensor for stretchable electronic skins IEEE Sensors J. 9 2008-9
16. Alirezaei H, Nagakubo A and Kuniyoshi Y 2007 A highly stretchable tactile distribution sensor for smooth surfaced humanoids Proc. IEEE-RAS Int. Conf. on Humanoid Robots (ICHR '07) (Pittsburgh, Pa., November 2007) pp 167-73
17. Ventrelli L, Beccai L, Mattoli V, Menciassi A and Dario P 2009 Development of a stretchable skin-like tactile sensor based on polymeric composites Proc. IEEE Int. Conf. on Robotics and Biomimetics (ROBIO '09) (Guilin, China, December 2009) pp 123-8
18. Lacasse M-A, Duchaine V and Gosselin C 2010 Characterization of the electrical resistance of carbon-black-filled silicone: application to a flexible and stretchable robot skin Proc. IEEE Int. Conf. on Robotics and Automation (ICRA '10) (Anchorage, Ak., May 2010) pp 4842-8
19. Wettels N, Santos V J, Johansson R S and Loeb G E 2008 Biomimetic tactile sensor array Adv. Robot. 22 829-49
20. Tseng W-Y, Fisher J S, Prieto J L, Rinaldi K, Alapati G and Lee A P 2009 A slow-adapting microfluidic-based tactile sensor J. Micromech. Microeng. 19 085002
21. Noda K, Iwase E, Matsumoto K and Shimoyama I 2010 Stretchable liquid tactile sensor for robot-joints Proc. IEEE Int. Conf. on Robotics and Automation (ICRA '10) (Anchorage, Ak., May 2010) pp 4212-7
22. Takei K, Takahashi T, Ho J C, Ko H, Gillies A G, Leu P W, Fearing R S and Javey A 2010 Nanowire active-matrix circuitry for low-voltage macroscale artificial skin Nature Mater. 9 821-6
23. Whitney R J 1949 The measurement of changes in human limb-volume by means of a mercury-in-rubber strain gauge Proc. Physiol. Soc. 109 5-6
24. Rastrelli L U, Anderson E L and Michie J D 1967 Elastomeric strain gauge U.S. Pat. No. 3,304,528
25. Pique A, Chrisey D B, Fitz-Gerald J M, McGill R A, Auyeung R C Y, Wu H D, Lakeou S, Nguyen V, Chung R and Duignan M 1967 Direct writing of electronic and sensor materials using a laser transfer technique J. Mater. Res. 15 1872-5
26. Menon R, Patel A, Gil D and Smith H I 2005 Maskless lithography Mater. Today 8 26-33
27. Xia Y and Whitesides G M 1998 Soft lithography Annu. Rev. Mater. Sci. 28 153-84
28. Tada H, Paris P C and Irwin G R 2000 The Stress Analysis of Cracks Handbook 3rd edn (New York: ASME Press)
29. Anderson T L 2005 Fracture Mechanics: Fundamentals and Applications 3rd edn (Boca Raton, Fla.: Taylor and Francis)

30. Anderson T L 2005 Theory of Elasticity 3rd edn (New York: McGraw-Hill)
31. Tajima R, Kagami S, Inaba M, and Inoue H, "Development of soft and distributed tactile sensors and the application to a humanoid robot," Adv. Rob., vol. 16, no. 4, pp. 381-397, 2002.
32. Park Y-L, Ryu S C, Black R J, Chau K, Moslehi B, and Cutkosky M R, "Exoskeletal force-sensing end-effectors with embedded optical fiber-bragg-grating sensors," IEEE Trans. Rob., vol. 25, no. 6, pp. 1319-1331, December 2009.
33. Park Y-L, Chen B, Young D, Stirling L, Wood R J, Goldfield E, and Nagpal R, "Bio-inspired active soft orthotic device for ankle foot pathologies," in Proc. IEEE/RSJ Int. Conf. Intell. Rob. Syst., San Francisco, Calif., September 2011.
34. Park Y-L, Majidi C, Kramer R, Berard P, and Wood R J, "Hyperelastic pressure sensing with a liquid-embedded elastomer," J. Micromech. Microeng., vol. 20, no. 12, 2010.
35. Herr H M and Kornbluh R D, "New horizons for orthotic and prosthetic technology: artificial muscle for ambulation," in Proc. SPIE, vol. 5385, 2004, pp. 1-9.

What is claimed:

1. A joint sensor for sensing an angle of a first limb with respect to second limb, wherein both limbs are connected to the joint, the joint sensor comprising:
   an elastic strain sensor adapted to sense strain along a strain axis, having a first end at a first position along the strain axis and a second end at a second position that is a first distance from the first position;
   wherein the elastic strain sensor includes two or more channels, each extending from a first end to a second end along the strain axis and a loop portion connecting the first end of a first channel to the first end of a second channel, wherein the loop portion has a substantially large cross-sectional area along an axis transverse to the strain axis, and a conductive liquid extending continuously from at least the second end of the first channel, the loop portion, to the second end of the second channel;
   wherein the first end of the elastic strain sensor is configured to be worn on the first limb and the second end of the elastic strain sensor is configured to be worn on the second limb, such that the elastic strain sensor becomes elongated when the joint is flexed and causes a change in resistance of the conductive liquid measured from the second end of the first channel to the second end of the second channel and the angle of the joint can be determined as a function of the resistance of the conductive liquid measured from the second end of the first channel to the second end of the second channel.

2. The joint sensor according to claim 1 wherein the elastic strain sensor is attached to a brace adapted to be worn on the first limb and the second limb.

3. The joint sensor according to claim 2 wherein the brace is a flexible brace.

4. The joint sensor according to claim 1 wherein the elastic strain sensor is attached to an article of clothing adapted to be worn on the first limb and the second limb.

5. The joint sensor according to claim 1 wherein the elastic strain sensor is connected to a computer whereby an output of the elastic strain sensor is input to the computer and the computer determines limb motion.

6. The joint sensor according to claim 1 wherein the elastic strain sensor is connected to a computer whereby an output of the elastic strain sensor is input to the computer and the computer determines changes in joint angle.

7. The joint sensor according to claim 1 wherein the elastic strain sensor is connected to a computer whereby an output of the elastic strain sensor is input to the computer and software running on the computer is controlled by the output of the elastic strain sensor.

8. A system comprising one or more joint sensors according claim 1, wherein each elastic strain sensor of each joint sensor is connected to a computer whereby an output of each two or more elastic strain sensors is input to the computer and software running on the computer is controlled by the output of at least one of the elastic strain sensors.

* * * * *